(12) United States Patent
Platenkamp et al.

(10) Patent No.: US 11,160,728 B2
(45) Date of Patent: Nov. 2, 2021

(54) MEDICAL CONTAINERS AND SYSTEM COMPONENTS WITH NON-DEHP PLASTICIZERS FOR STORING RED BLOOD CELL PRODUCTS, PLASMA AND PLATELETS

(71) Applicant: Fresenius Kabi Deutschland GmbH, Bad Homburg (DE)

(72) Inventors: Karin Platenkamp, Enschede (NL); Craig L. Sandford, Buffalo Grove, IL (US); Koos Hakvoort, Emmen (NL)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/118,396

(22) PCT Filed: Dec. 17, 2014

(86) PCT No.: PCT/EP2014/078127
§ 371 (c)(1),
(2) Date: Aug. 11, 2016

(87) PCT Pub. No.: WO2015/124236
PCT Pub. Date: Aug. 27, 2015

(65) Prior Publication Data
US 2017/0172847 A1 Jun. 22, 2017

(30) Foreign Application Priority Data
Feb. 20, 2014 (EP) ..................................... 14155899

(51) Int. Cl.
*A61J 1/14* (2006.01)
*A61M 1/02* (2006.01)
(Continued)

(52) U.S. Cl.
CPC ............... *A61J 1/1468* (2015.05); *A61J 1/10* (2013.01); *A61J 1/1475* (2013.01); *A61J 1/18* (2013.01);
(Continued)

(58) Field of Classification Search
CPC .......... A61J 1/10; A61J 1/1468; A61J 1/1475; A61J 1/18; A61J 1/201; A61J 1/2037;
(Continued)

(56) References Cited

U.S. PATENT DOCUMENTS 3,384,607 A 5/1968 Magne et al.
4,140,162 A 2/1979 Gajewski et al.
(Continued)

FOREIGN PATENT DOCUMENTS

CN 1273129 A 11/2000
CN 101215398 A 7/2008
(Continued)

OTHER PUBLICATIONS

International Search Report from PCT/EP2014/078127 dated Jun. 2, 2015.
(Continued)

*Primary Examiner* — Adam Marcetich
(74) *Attorney, Agent, or Firm* — Cook Alex Ltd.

(57) ABSTRACT

A container for blood or a blood component is provided, the container comprising one or more container walls defining an interior chamber, the container walls comprising one or more layers, the layers comprising or consisting of a composition comprising one or more polymeric materials and at least one extractable agent selected from the group consisting of a terephthalate ester, a cyclohexane dicarboxylic acid ester, a citrate ester, and a polyol ester, wherein the container further comprises one or more additional components, wherein the container comprises less than about 3% (w/w)

(Continued)

of di-2-ethylhexyl phthalate (DEHP), preferably wherein the container comprises less than about 3% (w/w) of phthalates. Thereby, improved blood products are provided in which the DEHP or overall phthalate content is reduced.

23 Claims, 5 Drawing Sheets

(51) Int. Cl.
| | | |
|---|---|---|
| *A61J 1/10* | (2006.01) | |
| *C08K 5/10* | (2006.01) | |
| *A61J 1/20* | (2006.01) | |
| *A61J 1/18* | (2006.01) | |
| *C08K 5/11* | (2006.01) | |
| *C08K 5/12* | (2006.01) | |

(52) U.S. Cl.
CPC .............. *A61J 1/201* (2015.05); *A61J 1/2037* (2015.05); *A61J 1/2048* (2015.05); *A61M 1/0209* (2013.01); *C08K 5/10* (2013.01); *C08K 5/11* (2013.01); *C08K 5/12* (2013.01); *C08K 2201/014* (2013.01); *C08K 2201/019* (2013.01)

(58) Field of Classification Search
CPC ................ A61J 1/2048; A61M 1/0209; C08K 2201/014; C08K 2201/019; C08K 5/10; C08K 5/11; C08K 5/12; C08L 27/06
See application file for complete search history.

(56) References Cited

U.S. PATENT DOCUMENTS

| | | | |
|---|---|---|---|
| 4,286,597 A | 9/1981 | Gajewski et al. | |
| 4,300,559 A | 11/1981 | Gajewski | |
| 4,301,800 A | 11/1981 | Collins | |
| 4,326,025 A | 4/1982 | Buckles | |
| 4,375,509 A | 3/1983 | Buckles | |
| 4,451,259 A | 5/1984 | Geissler | |
| 4,505,708 A | 3/1985 | Gajewski et al. | |
| 4,507,123 A | 3/1985 | Yoshida | |
| 4,507,387 A | 3/1985 | Gajewski | |
| 4,657,541 A | 4/1987 | Ichikawa et al. | |
| 4,670,013 A | 6/1987 | Barnes et al. | |
| 4,789,700 A | 12/1988 | Hull et al. | |
| 4,943,287 A | 7/1990 | Carmen | |
| 5,026,347 A | 6/1991 | Patel | |
| 5,079,002 A | 1/1992 | Naqal | |
| 5,100,401 A | 3/1992 | Patel | |
| 5,236,716 A | 8/1993 | Carmen et al. | |
| 5,248,531 A | 9/1993 | Naqal | |
| 5,252,373 A | 10/1993 | Ganske et al. | |
| 5,382,526 A | 1/1995 | Gajewski et al. | |
| 5,637,819 A | 6/1997 | Rogers | |
| 5,713,694 A | 2/1998 | Monda et al. | |
| 5,721,024 A | 2/1998 | Carmen et al. | |
| 5,769,839 A | 6/1998 | Carmen et al. | |
| 5,772,960 A | 6/1998 | Ito et al. | |
| 5,824,216 A | 10/1998 | Joie et al. | |
| 5,849,843 A | 12/1998 | Laurin et al. | |
| 5,955,519 A | 9/1999 | Neri et al. | |
| 6,046,274 A | 4/2000 | Grandjean et al. | |
| 6,150,085 A | 11/2000 | Hess et al. | |
| 6,162,396 A | 12/2000 | Bitensky et al. | |
| 6,468,258 B1 | 10/2002 | Shang | |
| 6,579,583 B2 | 6/2003 | Patel | |
| 6,675,560 B2 | 1/2004 | Gott et al. | |
| 7,208,545 B1 | 4/2007 | Branner et al. | |
| 7,276,621 B2 | 10/2007 | Cook et al. | |
| 7,297,738 B2 | 11/2007 | Gosse et al. | |
| 7,595,421 B2 | 9/2009 | Grass et al. | |
| 7,629,413 B2 | 12/2009 | Goodwin et al. | |
| 7,754,198 B2 | 7/2010 | Whitehead et al. | |
| 7,786,201 B2 | 8/2010 | Grass et al. | |
| 7,964,658 B2 | 6/2011 | Grass | |
| 8,026,314 B2 | 9/2011 | Hansel et al. | |
| 8,283,411 B2 | 10/2012 | Gosse et al. | |
| 8,329,796 B2 | 12/2012 | Grass et al. | |
| 8,372,912 B2 | 2/2013 | Olsen et al. | |
| 8,568,846 B2 | 10/2013 | Dakka et al. | |
| 8,669,311 B2 | 3/2014 | Colle et al. | |
| 9,828,488 B2 | 11/2017 | Sakai | |
| 10,398,625 B2 | 9/2019 | Sandford et al. | |
| 2003/0014948 A1 | 1/2003 | Gott et al. | |
| 2003/0157150 A1 | 8/2003 | Lee et al. | |
| 2004/0078022 A1* | 4/2004 | Donart ........................ | A61J 1/05 604/408 |
| 2005/0020718 A1* | 1/2005 | Gosse .................. | C08K 5/0016 523/105 |
| 2007/0027244 A1* | 2/2007 | Schar ...................... | C08K 5/521 524/306 |
| 2007/0037926 A1 | 2/2007 | Olsen et al. | |
| 2007/0135562 A1 | 6/2007 | Freese et al. | |
| 2007/0293646 A1* | 12/2007 | Gosse .................... | C08K 5/12 526/344 |
| 2008/0132712 A1 | 6/2008 | Denoux et al. | |
| 2008/0183004 A1 | 7/2008 | Shieh et al. | |
| 2008/0200595 A1 | 8/2008 | Hinault et al. | |
| 2009/0149586 A1 | 6/2009 | De Quadros Junior et al. | |
| 2009/0239208 A1* | 9/2009 | Mayaudon ................ | A01N 1/02 435/2 |
| 2009/0277532 A1 | 11/2009 | Neas et al. | |
| 2009/0287007 A1 | 11/2009 | Abraham et al. | |
| 2010/0042066 A1 | 2/2010 | Kulhein et al. | |
| 2010/0298477 A1* | 11/2010 | Godwin .................. | C08L 27/06 524/285 |
| 2010/0305255 A1 | 12/2010 | Grass | |
| 2011/0021680 A1* | 1/2011 | Colle ...................... | C08K 5/103 524/313 |
| 2011/0028624 A1 | 2/2011 | Arendt et al. | |
| 2011/0065860 A1 | 3/2011 | Hidalgo et al. | |
| 2011/0097563 A1 | 4/2011 | Sandford et al. | |
| 2011/0098390 A1 | 4/2011 | Dakka et al. | |
| 2011/0117647 A1 | 5/2011 | Mayaudon et al. | |
| 2011/0281987 A1* | 11/2011 | Godwin .................. | C08K 5/12 524/291 |
| 2012/0022197 A2 | 1/2012 | Dakka et al. | |
| 2012/0329036 A1 | 12/2012 | Hess et al. | |
| 2013/0011824 A1 | 1/2013 | Chan et al. | |
| 2013/0018353 A1 | 1/2013 | Chung et al. | |
| 2013/0137789 A1 | 5/2013 | Olsen et al. | |
| 2013/0154151 A1* | 6/2013 | Wang ...................... | B29C 48/92 264/177.1 |
| 2013/0171385 A1 | 7/2013 | Dakka et al. | |
| 2013/0303640 A1 | 11/2013 | Kim et al. | |
| 2013/0310471 A1* | 11/2013 | Becker .................. | C08J 9/0023 521/73 |
| 2013/0310472 A1 | 11/2013 | Becker et al. | |
| 2013/0310473 A1 | 11/2013 | Becker et al. | |
| 2013/0317152 A1 | 11/2013 | Becker et al. | |
| 2013/0317153 A1* | 11/2013 | Grass ...................... | C08K 5/12 524/296 |
| 2013/0331491 A1 | 12/2013 | Becker et al. | |
| 2013/0338276 A1* | 12/2013 | Becker .................. | C07D 307/68 524/111 |
| 2014/0016883 A1 | 1/2014 | Van Waeg et al. | |
| 2014/0024754 A1 | 1/2014 | Becker et al. | |
| 2014/0086892 A1 | 3/2014 | Min et al. | |
| 2014/0091047 A1 | 4/2014 | Radwanski et al. | |
| 2014/0162045 A1 | 6/2014 | Bourassa et al. | |
| 2014/0205778 A1* | 7/2014 | Sakai ...................... | C08K 5/12 428/35.2 |
| 2014/0276527 A1 | 9/2014 | Sandford et al. | |
| 2014/0309345 A1* | 10/2014 | Frenkel ................ | C08K 5/1515 524/109 |
| 2014/0336319 A1* | 11/2014 | Kim ........................ | C07C 67/40 524/293 |
| 2015/0190309 A1* | 7/2015 | Zia ........................ | A01N 1/0226 435/2 |

(56) References Cited

U.S. PATENT DOCUMENTS

| | | | | |
|---|---|---|---|---|
| 2015/0225537 | A1* | 8/2015 | L'Abbe | C07C 69/40 |
| | | | | 524/296 |
| 2015/0232411 | A1* | 8/2015 | Storzum | C07C 69/82 |
| | | | | 524/297 |
| 2016/0215119 | A1* | 7/2016 | Wagner | C08K 5/1535 |

FOREIGN PATENT DOCUMENTS

| | | |
|---|---|---|
| CN | 101798428 A | 8/2010 |
| CN | 101979434 A | 2/2011 |
| CN | 102503975 A | 6/2012 |
| CN | 102634127 A | 8/2012 |
| CN | 103642150 A | 3/2014 |
| DE | 3200 264 | 7/1983 |
| DE | 3444155 A1 | 6/1985 |
| DE | 4022700 | 1/1992 |
| DE | 202010004386 U1 | 6/2010 |
| DE | 10 2010 003415 | 10/2011 |
| DE | 102010003415 A1 | 10/2011 |
| DE | 202013105795 U1 | 2/2014 |
| EP | 0 026 912 A2 | 4/1981 |
| EP | 0 340 305 A1 | 11/1989 |
| EP | 0 420 757 | 4/1991 |
| EP | 0138147 | 4/1993 |
| EP | 0829267 | 8/2001 |
| EP | 0778030 | 10/2001 |
| EP | 1864964 | 12/2007 |
| EP | 1432758 | 11/2008 |
| EP | 2114854 | 11/2009 |
| EP | 1309450 | 1/2011 |
| EP | 2599766 | 6/2013 |
| EP | 2089210 | 10/2013 |
| EP | 2665358 | 11/2013 |
| EP | 2666819 | 11/2013 |
| EP | 2220154 | 6/2014 |
| EP | 2777393 | 9/2014 |
| EP | 2810982 | 12/2014 |
| GB | 1172743 A | 12/1969 |
| GB | 1279939 A | 6/1972 |
| IN | 2006CH00254 | 2/2006 |
| IN | 1407CHE2008 | 6/2010 |
| JP | S58162649 A | 9/1983 |
| JP | S5933343 A | 2/1984 |
| JP | S6023621 A | 2/1985 |
| JP | H067450 A | 1/1994 |
| JP | H0824329 A | 1/1996 |
| JP | H0827341 A | 1/1996 |
| JP | H09194818 | 7/1997 |
| JP | H1149909 A | 2/1999 |
| JP | 2003-171288 | 6/2003 |
| JP | 2003165881 A | 6/2003 |
| JP | 2003226788 A | 8/2003 |
| JP | 2003253072 A | 9/2003 |
| JP | 2008074955 A | 4/2008 |
| JP | 2014-223182 | 12/2014 |
| JP | 2014223182 A | 12/2014 |
| JP | 2015089931 A | 5/2015 |
| JP | 5933343 B2 | 6/2016 |
| WO | WO 1993/014810 | 8/1993 |
| WO | WO 9614741 | 5/1996 |
| WO | WO 99/03921 | 1/1999 |
| WO | WO 2003/029339 A1 | 4/2003 |
| WO | WO2009/085453 | 7/2009 |
| WO | WO 2009/118261 | 10/2009 |
| WO | WO2011004390 A2 | 1/2011 |
| WO | WO 2011/023590 A1 | 3/2011 |
| WO | WO 2011/110350 | 9/2011 |
| WO | WO 2012/094565 | 7/2012 |
| WO | WO 2012/113609 | 8/2012 |
| WO | WO 2012/169081 A1 | 12/2012 |
| WO | WO2013/006631 A1 | 1/2013 |
| WO | WO 2013/025277 | 2/2013 |
| WO | WO 2013/043658 | 3/2013 |
| WO | WO 2013/043711 | 3/2013 |
| WO | WO 2013/084707 A1 | 6/2013 |
| WO | WO 2013/100875 | 7/2013 |
| WO | WO 2013/123127 | 8/2013 |
| WO | WO 2014/028481 | 2/2014 |
| WO | WO 2014/031852 | 2/2014 |
| WO | WO 2014/076717 | 5/2014 |
| WO | WO 2014/093438 | 6/2014 |
| WO | WO 2014/135055 | 9/2014 |
| WO | WO 2014/185872 | 11/2014 |
| WO | WO 2014/195055 | 12/2014 |
| WO | WO 2014/195056 | 12/2014 |

OTHER PUBLICATIONS

European Extended Seach Report dated Jul. 18, 2014 for EP Application No. 13194083.5-1660.
International Preliminary Report on Patentability and Written Opinion dated Mar. 25, 2014 for International Application No. PCT/US2012/056100.
International Search Report dated Dec. 12, 2012 for International Application No. PCT/US2012/056100.
Chembumukulam, S.B. et al., PVC Containers for Collection and Storage of Blood and Blood Components. WPI/Thomson, vol. 2008, No. 17, Dec. 28, 2007, XP 002617312 . . . Indian Patent Appln. No. IN2006CH00254.
Database WPI, Week 200403, Thomson Scientific, London, GB; AN 2004-026123, XP002688187 & JP 2003-171288 A Terumo Corp. Jun. 17, 2003 Abstract.
Davey, R.J., et al., Characteristics of White Cell-reduced Red Cells Stored in Tri-(2-ethylhexyl)trimellitate Plastic. Transfusion. Oct. 1994, vol. 34(10): pp. 895-8 (abstract).
Draper, C.J. et al., Biochemical and Structural Changes in RBCs Stored with Different Plasticizers: The Role of Hexanol. Transfusion. vol. 42, No. 7, Jul. 1, 2002, pp. 830-835, XP55045604.
Dumont, Larry J., et al., Exploratory in Vitro Study of Red Blood Cell Storage Containers Formulated with an Alternative Plasticizer. Transfusion. vol. 52, No. 7, dated Dec. 30, 2011, pp. 1439-1445, XP055127658 ISSN : 0041-1132, DOI.
Folarin, O.M. and Sadiku, E.R., Thermal Stabilizers for Poly(vinyl chloride): A Review. International Journal of Physical Sciences. 2011. vol. 6, No. 18, pp. 4323-4330.
Hill, H.R. et al., The Effects of Polyvinyl Chloride and Polyolefin Blood Bags on Red Blood Cells Stored in a new Additive Solution. Vox Sanguinis, vol. 81, No. 3, Oct. 1, 2001, pp. 161-166.
Simmchen, J. et al., Progress in the Removal of Di-[2-Ethylhexyl]-Phthalate as Plasticizer in Blood Bags, vol. 26, No. 1, dated Jan. 1, 2012, pp. 27-37, XP028338542, ISSN: 0887-7963, DOI: 10.1016/J.TMRV.2011.06.001.
Yuji, Haishima, et al., Screening Study on Hemolysis Suppression Effect of an Alternative Plasticizer for the Development of a Novel Blood Container Made of Polyvinyl Chloride, Journal of Biomedical Materials Research. vol. 102, No. 4, 2013. pp. 721-728.
Benaniba et al., "Stabilization of PVC by Epoxidized Sunflower Oil in the Presence of Zinc and Calcium Stearates", Polymer Degradation and Stability, 2003, pp. 245-249, vol. 82, No. 2.
Bui et al., "Human Exposure, Hazard and Risk of Alternative Plasticizers to Phthalate Esters", Science of the Total Environment, Jan. 2016, pp. 451-467, vol. 541.
Opinion on the Safety of Medical Devices Containing DEHP-Plasticized PVC or Other Plasticizers on Neonates and Other Groups Possibly at Risk by SCENIHR dated Feb. 6, 2008.
Opposition filed in Application EP2791425 for "Red Blood Cell Products and the Storage of Red Blood Cells in Containers Free of Phtalate Plasticizers" Dated Jul. 5, 2018.
Radwanski, Et Al., Abstract from the AABB Annual Meeting of Presentation E-Sol 5 Additive Solutions Improves Storage of Red Blood Cells in DINCH Plasticized PVC Storage Containers:, Dated Sep. 12, 2011.
BASF, HEXAMOLL * DINCH Safety Data Sheet, Dated Nov. 13, 2007.
Bibliographic Sheet from The Patent Office Journal, 5.14613, Dated Jun. 4, 2010.

(56) References Cited

OTHER PUBLICATIONS

Akzo Nobel brochure for "LANKOMARK LZB320", Dated Apr. 24, 2002.
Summons to Attend Oral Proceedings Pursuant to Rule 115(1) dated Sep. 9, 2019 for European Application No. 12766821.8.

* cited by examiner

MEDICAL CONTAINERS AND SYSTEM COMPONENTS WITH NON-DEHP PLASTICIZERS FOR STORING RED BLOOD CELL PRODUCTS, PLASMA AND PLATELETS

CROSS-REFERENCE TO RELATED APPLICATIONS

This is a U.S. national stage application of International Patent Application No. PCT/EP2014/078127, filed Dec. 17, 2014, which claims the benefit of and priority to EP Application Serial No. 14155899.9, filed Feb. 20, 2014, both of which are incorporated herein by reference.

FIELD OF THE INVENTION

The present invention relates to the field of blood banking and transfusion medicine. In particular, the present invention relates to systems, system components and containers for collecting, processing, storing and the transfusion of blood and blood components. The present invention also provides blood component products.

BACKGROUND

Donor blood is widely used in medical applications. Typically, whole blood collected from a donor is processed further. Often, the blood is processed to obtain blood components such as red blood cells (RBCs), plasma and platelets.

This can for example be done by collection of whole blood, followed by filtration and subsequently by centrifugation, by collection of whole blood, followed by centrifugation and subsequently by filtration, or by the automated collection of components.

RBCs are often separated from collected whole blood and transfused later to a patient in need thereof. For example, RBCs may be administered to a patient suffering from a loss of blood due to trauma, as a post-chemotherapy treatment, or as part of a treatment for one or more blood-borne diseases. Unless administered immediately after collection and separation, RBCs are typically stored for some period of time prior to transfusion. The storage period may vary from a few days to several weeks.

Plasma is commonly used for direct transfusion (as fresh frozen plasma, hereinafter "FFP"), for fractionation, and as an additive solution for platelet concentrates. FFP and fractionated plasma may be administered to a patient in need of plasma coagulation factors or intravascular volume when this patient is suffering from e.g. trauma coagulation disorders, cardiopulmonary bypass surgery, or chronic heparinization regimes. Like RBCs, plasma is frequently stored for some period of time prior to transfusion. The storage period of plasma may vary from several months to up to two years. The storage period of plasma as platelet additive solution may last up to seven days.

Persons with not enough or not sufficiently functioning platelets can suffer from spontaneous hemorrhages that mainly occur in the skin and mucous membranes but sometimes also internally. These hemorrhages can be caused by e.g. cancer treatments and trauma coagulation disorders. Thus, platelet transfusions are for example used to avoid these spontaneous and sometimes life-threatening hemorrhages. Prior to use, platelets are frequently stored, often for a short period of up to 7 days.

Per European legislation, collected whole blood must be processed and transferred into the final storage containers within 24 hours. This time lapse allows for logistic benefits, as well as an increased yield of platelets. Preferably, the whole blood is stored at ambient temperature and not refrigerated to allow for the harvesting of platelets.

However, intermediate storage at room temperature may also increase lesions of RBCs, and hemolysis may occur.

Since years, blood banks and hospitals have been using plasticized polyvinylchloride (PVC)-based materials and solutions for collecting, processing, storing and transfusing blood and blood components.

Due to its properties, PVC is highly preferred for these applications, in particular for the use in transfusion systems. However, PVC is rather brittle and therefore is used along with a plasticizer or extractable agent to ensure the required flexibility and softness of the material. Thus typically, ortho-phthalates (hereinafter also designated as "phthalates") such as di-2-ethylhexyl phthalate (DEHP) are used as plasticizer or extractable agent for PVC.

For many reasons, the use of DEHP yields excellent results for the plasticization of PVC. Because DEHP is very compatible with PVC, a homogenous compound can be easily produced for the extrusion of foils, the extrusion of tubes, and the injection molding of components at temperatures, pressures, and durations of heating that do not cause a significant degradation of the PVC. Opposite to more technical fields of the application of PVC, medical device regulations limit the use of antioxidants as well as PVC stabilizers to further limit the degradation of PVC.

Another reason why DEHP is so widely used as plasticizer for PVC in the field is that DEHP exhibits a positive impact on RBC quality during storage. It is known that storage of RBCs can negatively affect RBC function. One problem typically encountered is the occurrence of hemolysis in stored RBCs. An acceptable level of hemolysis is below 1.0% at the end of the storage period for registration purposes in, for example, the U.S., and below 0.8% at the end of the storage period in, for example, the E.U. A level of hemolysis of below 0.4% on average is found acceptable by most blood banks and transfusion centers. DEHP has been reported to reduce hemolysis (Rock et al. "Incorporation of plasticizer into red cells during storage", Transfusion, 1984; Horowitz et al. "Stabilization of RBCs by the Plasticizer, Di(ethylhexyl)phthalate" Vox Sanguinis, 1985). This effect has been attributed to leaching of DEHP from the storage container.

Considering hemolysis reduction, DEHP and PVC-DEHP storage containers have been found to work well in combination with commonly used additive solutions for RBC storage, such as SAG-M (Saline, Adenine, Glucose, Mannitol) or AS-1 (of similar composition, commercially available as Adsol through Fenwal Inc., Lake Zurich, Ill., United States).

However, adverse health effects of phthalates, in particular DEHP, have been reported in rodents, resulting in concern for human exposure to this material. Certain recipients of blood or blood components are considered particularly sensitive to the plasticizer DEHP, such as pregnant women and neonates, because of the greater potential for interaction.

In the E.U, for example, because of these concerns, if the percentage of DEHP, which is therein classified as a reproductive toxin class 1B, in a medical device exceeds 0.1% w/w in a solid or liquid, the item must carry a phthalate warning symbol. 1272/2008 Annex VI.

Thus, while the leaching of the DEHP plasticizer from the used materials on the one hand may have a positive impact on the quality of blood components, there is an increasing need to provide blood and blood components that are essentially DEHP-free (or more preferably essentially phthalate-free) to individuals in need thereof.

Since the main exposure of blood components to DEHP and phthalates in general is believed to occur due to leaching from container walls during storage of blood or blood components in dedicated containers, there have been attempts in the prior art to reduce the DEHP or phthalate content in the large contact surfaces formed by sheet or foil materials used for the walls of storage containers. However typically, container components such as injection-molded components (often 2-3 per container) and tube inserts are still made of PVC-DEHP.

One approach taken was to substitute PVC in sheet layers of medical containers with alternative materials that are less brittle and therefore allow to use lower amounts of plasticizers.

However, PVC offers a number of advantages that make its use in the handling and storage of blood and blood component products desirable. For example, PVC is very durable, well suited for sterilizing and storing aqueous solutions, resistant to alcohol frequently comprised in commercially available disinfectants, and can be sterile-docked to prevent any incorporation of bacteria when tubes are connected before or after storage.

Another approach has been to use alternative, non-DEHP plasticizers in the sheeting of storage containers.

However, while the prior art has focused on the problem of DEHP or phthalate leaching from storage container walls, residual DEHP or phthalates in donor blood and blood components are nevertheless observed and remain a problem in respect of product safety.

Moreover, the reduction or substitution of DEHP, or phthalates in general, in the walls of storage containers may result in problems with increased hemolysis, which may adversely affect product quality and storage time.

Therefore, there is a need for improved blood products in which the DEHP or overall phthalate content is further reduced. There is also a need for improved materials and systems as well as additive solutions that can be used in relation therewith.

SUMMARY

The present invention provides for a container for blood or a blood component, the container comprising one or more container walls defining an interior chamber, the container walls comprising one or more layers, the layers comprising or consisting of a composition comprising one or more polymeric materials and at least one extractable agent selected from the group consisting of a terephthalate ester, a cyclohexane dicarboxylic acid ester, a citrate ester, and a polyol ester, wherein the container further comprises one or more additional components, wherein the container comprises less than about 3% (w/w) of di-2-ethylhexyl phthalate (DEHP), preferably wherein the container comprises less than about 3% (w/w) of phthalates.

The container may be a container wherein at least one of the one or more layers consists of a composition comprising polyvinylchloride (PVC), preferably wherein at least one of the one or more layers consists of a composition comprising one polymeric material, the one polymeric material being PVC, more preferably wherein all of the one or more layers consist of a composition comprising one polymeric material, the one polymeric material being PVC.

The container may be a container wherein the terephthalate ester is di-2-ethyl hexyl terephthalate (DEHT), the cyclohexane dicarboxylic acid ester is 1,2-cyclohexane dicarboxylic acid diisononyl ester (DINCH) or 1,2-cyclohexyl dicarboxylic acid di-2-ethylhexyl ester (DEHCH), the citrate ester is selected from acetyl tributyl citrate (ATBC), acetyl trihexyl citrate (ATHC), and butiryl trihexyl citrate (BTHC), and the polyol ester is pentaerythritol tetravalerate.

The container may be a container wherein the composition of the layers comprises a second extractable agent, preferably a second extractable agent selected from the group consisting of a terephthalate ester, a cyclohexane dicarboxylic acid ester, a citrate ester, and a polyol ester, and optionally, a third extractable agent, preferably a third extractable agent selected from the group consisting of a terephthalate ester, a cyclohexane dicarboxylic acid ester, a citrate ester, and a polyol ester.

The container may be a container wherein the container walls comprise at least a first layer and a second layer, wherein the first layer consists of a composition comprising one or more polymeric materials and at least a first extractable agent selected from the group consisting of a terephthalate ester, a cyclohexane dicarboxylic acid ester, a citrate ester, and a polyol ester, wherein the second layer consists of a composition comprising one or more polymeric materials and at least a second extractable agent selected from the group consisting of a terephthalate ester, a cyclohexane dicarboxylic acid ester, a citrate ester, and a polyol ester, the container optionally comprising a third layer, the third layer consisting of a composition comprising one or more polymeric materials and at least a third extractable agent selected from the group consisting of a terephthalate ester, a cyclohexane dicarboxylic acid ester, a citrate ester, and a polyol ester, wherein the first, the second and optionally, the third extractable agent are the same, or are different from each other.

The container may be a container wherein the first extractable agent is a terephthalate ester, preferably DEHT, and the second extractable agent is selected from the group consisting of a citrate ester, preferably ATBC or BTHC, a cyclohexane dicarboxylic acid ester, preferably DINCH, and a polyol ester, preferably pentaerythritol tetravalerate, or wherein the first extractable agent is a cyclohexane dicarboxylic acid ester, preferably DINCH, and the second extractable agent is selected from the group consisting of a citrate ester, preferably ATBC or BTHC, a terephthalate ester, preferably DEHT, and a polyol ester, preferably pentaerythritol tetravalerate or wherein the first extractable agent is a citrate ester, preferably ATBC, and the second extractable agent is selected from the group consisting of a terephthalate ester, preferably DEHT, a citrate ester, preferably BTHC, a cyclohexane dicarboxylic acid ester, preferably DINCH, and a polyol ester, preferably pentaerythritol tetravalerate, or wherein the first extractable agent is a citrate ester, preferably BTHC, and the second extractable agent is selected from the group consisting of a terephthalate ester, preferably DEHT, a citrate ester, preferably ATBC, a cyclohexane dicarboxylic acid ester, preferably DINCH, and a polyol ester, preferably pentaerythritol tetravalerate, or wherein the first extractable agent is a polyol ester, preferably pentaerythritol tetravalerate, and the second extractable agent is selected from the group consisting of a terephthalate ester, preferably DEHT, a citrate ester, preferably ATBC or BTHC, and a cyclohexane dicarboxylic acid ester, preferably DINCH.

The container may be a container wherein the first extractable agent is DEHT and the second extractable agent is DINCH, or wherein the first extractable agent is DEHT and the second extractable agent is ATBC, or wherein the first extractable agent is DEHT and the second extractable agent is BTHC, or wherein the first extractable agent is DEHT and the second extractable agent is pentaerythritol tetravalerate, or wherein the first extractable agent is DINCH and the second extractable agent is ATBC, or wherein the first extractable agent is DINCH and the second extractable agent is BTHC, or wherein the first extractable agent is DINCH and the second extractable agent is pentaerythritol tetravalerate.

The container may be a container wherein the one or more additional components comprise or consist of a composition comprising one or more polymeric materials and at least one extractable agent selected from the group consisting of a terephthalate ester, a cyclohexane dicarboxylic acid ester, a citrate ester, and a polyol ester, wherein the additional components comprise less than about 3% (w/w) of DEHP, preferably wherein the additional components comprise less than about 3% (w/w) of phthalates.

The container may be a container wherein the composition of the one or more layers and the composition of the one or more additional components are selected independently from each other.

The container may be a container, wherein the additional component comprises or consists of a composition comprising polyvinylchloride (PVC), preferably wherein the composition comprises one polymeric material, the one polymeric material being PVC.

The container may be a container wherein the composition of the one or more additional components comprises a second extractable agent, preferably a second extractable agent selected from the group consisting of a terephthalate ester, a cyclohexane dicarboxylic acid ester, a citrate ester, and a polyol ester, and optionally, a third extractable agent, preferably a third extractable agent selected from the group consisting of a terephthalate ester, a cyclohexane dicarboxylic acid ester, a citrate ester, and a polyol ester.

The container may be a container wherein the composition of the one or more additional components comprises a first and a second extractable agent, wherein the first extractable agent is a terephthalate ester, preferably DEHT, and the second extractable agent is selected from the group consisting of a citrate ester, preferably ATBC or BTHC, a cyclohexane dicarboxylic acid ester, preferably DINCH, and a polyol ester, preferably pentaerythritol tetravalerate, or wherein the first extractable agent is a cyclohexane dicarboxylic acid ester, preferably DINCH, and the second extractable agent is selected from the group consisting of a citrate ester, preferably ATBC or BTHC, a terephthalate ester, preferably DEHT, and a polyol ester, preferably pentaerythritol tetravalerate, preferably wherein the first extractable agent is DEHT and the second extractable agent is DINCH, or wherein the first extractable agent is DEHT and the second extractable agent is ATBC, or wherein the first extractable agent is DEHT and the second extractable agent is BTHC, or wherein the first extractable agent is DEHT and the second extractable agent is pentaerythritol tetravalerate, or wherein the first extractable agent is DINCH and the second extractable agent is ATBC, or wherein the first extractable agent is DINCH and the second extractable agent is BTHC, or wherein the first extractable agent is DINCH and the second extractable agent is pentaerythritol tetravalerate, more preferably wherein the first extractable agent is DINCH and the second extractable agent is ATBC if the additional component is injection molded, and wherein the first extractable agent is DEHT and the second extractable agent is ATBC if the additional component is a tube.

The container may be a container wherein the additional component is selected from the group consisting of an outlet port, preferably a spike port, an inlet port preferably a tube insert or breaker port, an adapter, a spike, a seal, a valve, a tube, and a label, preferably a primary blood bag label, and combinations thereof, and/or wherein the additional component is an injection molded additional component, or an extruded additional component.

The present invention also provides for a system component for a system for blood or blood component collection, processing, storage and/or transfusion, the system component comprising or consisting of a composition comprising one or more polymeric materials and at least one extractable agent selected from the group consisting of a terephthalate ester, a cyclohexane dicarboxylic acid ester, a citrate ester, and a polyol ester, wherein the system component comprises less than about 3% (w/w) of DEHP, preferably wherein the system component comprises less than about 3% (w/w) of phthalates.

The system component may be a system component wherein the system component comprises or consists of a composition comprising polyvinylchloride (PVC), preferably wherein the composition comprises one polymeric material, the one polymeric material being PVC.

The system component may be a system component wherein the terephthalate ester is di-2-ethyl hexyl terephthalate (DEHT), the cyclohexane dicarboxylic acid ester is 1,2-cyclohexane dicarboxylic acid diisononyl ester (DINCH) or 1,2-cyclohexyl dicarboxylic acid di-2-ethylhexyl ester (DEHCH), the citrate ester is selected from acetyl tributyl citrate (ATBC), acetyl trihexyl citrate (ATHC), and butiryl trihexyl citrate (BTHC), and the polyol ester is pentaerythritol tetravalerate.

The system component may be a system component wherein the composition further comprises a second extractable agent, preferably a second extractable agent selected from the group consisting of a terephthalate ester, a cyclohexane dicarboxylic acid ester, a citrate ester, and a polyol ester, and optionally, further comprises a third extractable agent, preferably a third extractable agent selected from the group consisting of a terephthalate ester, a cyclohexane dicarboxylic acid ester, a citrate ester, and a polyol ester.

The system component may be a system component wherein the first extractable agent is a terephthalate ester, preferably DEHT, and the second extractable agent is selected from the group consisting of a citrate ester, preferably ATBC or BTHC, a cyclohexane dicarboxylic acid ester, preferably DINCH, and a polyol ester, preferably pentaerythritol tetravalerate, or wherein the first extractable agent is a cyclohexane dicarboxylic acid ester, preferably DINCH, and the second extractable agent is selected from the group consisting of a citrate ester, preferably ATBC or BTHC, a terephthalate ester, preferably DEHT, and a polyol ester, preferably pentaerythritol tetravalerate, preferably wherein the first extractable agent is DEHT and the second extractable agent is DINCH, or wherein the first extractable agent is DEHT and the second extractable agent is ATBC, or wherein the first extractable agent is DEHT and the second extractable agent is BTHC, or wherein the first extractable agent is DEHT and the second extractable agent is pentaerythritol tetravalerate, or wherein the first extractable agent is DINCH and the second extractable agent is ATBC, or wherein the first extractable agent is DINCH and the second extractable agent is BTHC, or wherein the first extractable agent is DINCH and the second extractable agent is pentaerythritol tetravalerate, more preferably wherein the first extractable agent is DINCH and the second extractable agent is ATBC if the system component is injection molded, and wherein the first extractable agent is DEHT and the second extractable agent is ATBC if the system component is a tube.

The system component may be a system component wherein the system component is selected from the group consisting of an outlet port, preferably a spike port, an inlet port preferably a tube insert or breaker port, an adapter, a spike, a seal, a valve, a tube, and a label, preferably a primary blood bag label, and combinations thereof, and/or wherein the system component is an injection molded system component, or an extruded system component.

The present invention also provides for a system for blood or blood component collection, processing, storage and/or transfusion, the system comprising at least one system component according to the invention, wherein the system comprises less than about 3% (w/w) of di-2-ethylhexyl phthalate, preferably wherein the system comprises less than about 3% (w/w) of phthalates.

The system may further comprise at least one container according to the invention.

The system may be a system wherein the composition of the system component is chosen independently from the compositions of the container layers.

The present invention also provides for a blood component product, the blood component product comprising: (a) a container according to the invention, (b) a blood component, and optionally (c) an additive solution, wherein the blood component product comprises less than about 3% (w/w) of DEHP, preferably wherein the blood component product comprises less than about 3% (w/w) of phthalates.

The blood component product may be a blood component product wherein the blood component is selected from the group consisting of red blood cells, plasma or platelets.

The blood component product may be a blood component product wherein the blood component is red blood cells and wherein the blood component product comprises an additive solution comprising a nutrient and a buffer.

The blood component product may be a blood component product wherein the additive solution is isotonic or hypotonic, preferably wherein the isotonic or hypotonic additive solution is phosphate buffered, more preferably wherein the additive solution is an isotonic phosphate buffered additive solution with a pH of about 7.0 or less, or a hypotonic phosphate buffered additive solution with a pH of about 7.0 or less or of at least about 8.0.

The blood component product may be a blood component product wherein the additive solution is an isotonic or hypotonic additive solution comprising about 0 mM to 70 about mM of sodium chloride, about 1 mM to about 4.0 mM of adenine and/or guanosine; about 20 mM to about 60 mM of mannitol; about 2 mM to about 40 mM of sodium citrate and/or citric acid; about 16 mM to about 30 mM of sodium phosphate dibasic and/or monobasic, and about 20 mM to about 140 mM of glucose, preferably wherein the additive solution is selected from PAGGS-M, PAGGC-M, and E-sol.

The blood component product may be a blood component product wherein the additive solution is a hypertonic additive solution and wherein the container is a container comprising at least two extractable agents selected from the group consisting of a terephthalate ester, a cyclohexane dicarboxylic acid ester, a citrate ester, and a polyol ester, as indicated above, preferably wherein the hypertonic additive solution is an additive solution comprising about 40 mM to about 120 mM glucose, about 1.2 mM to about 2.2 mM adenine, about 25 mM to about 45 mM mannitol, and about 140 mM to 160 mM of sodium chloride, more preferably wherein the additive solution selected from SAG-M and AS-1.

The blood component product may be a blood component product wherein the blood component is red blood cells and the container is a container comprising DEHT, DINCH or a combination thereof, or wherein the blood component is plasma and the container is a container comprising DEHT, DINCH or a combination thereof, or wherein the blood component is platelets and the container is a container comprising DINCH, BTHC, pentaerythritol tetravalerate, or a combination thereof.

Preferably, the container, system component, system, or blood component product according to the invention comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% or less, about 0.0005% (w/w) or less about 0.0001% or less, or about 0.0000% (w/w) of DEHP, preferably wherein the container, system component, system or blood component product comprises about 4% (w/w) or less, about 3.5% (w/w) or less, about 3% (w/w) or less, about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates, more preferably wherein the container, system component, system or blood component product is DEHP-free, or is phthalate-free.

DETAILED DESCRIPTION

Figure 1:
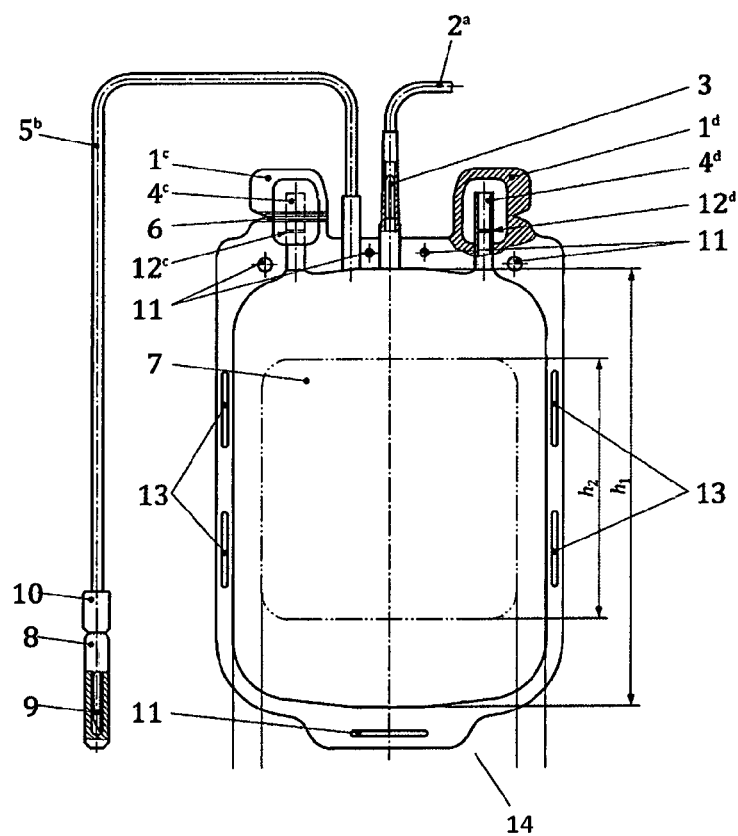
FIG. 1 shows an exemplary system according to the invention.

The invention is now described in more detail. Subsection headlines are for the convenience of the reader only and are not to be construed as limiting. References cited herein are incorporated in their entirety.

The present invention provides biocompatible containers, system components and systems for collecting, processing, storing and/or transfusing blood and blood components such as RBC, plasma, and platelets. The containers, system components and systems are essentially or entirely DEHP-free or phthalate-free. The invention furthermore provides improved blood component products that are essentially or entirely DEHP-free or phthalate-free.

The materials and compositions used according to the invention have good mechanical properties for the processing of whole blood and the freezing of plasma, have good gas permeation properties for the storage of platelets, and incorporate one or more extractable agents in amounts sufficient to suppress hemolysis. Advantageously, the materials and compositions are able to withstand steam sterilisation and gamma irradiation at bacteria-eliminating levels in the application of blood transfusion.

The advantageous properties of the materials and compositions according to the invention are achieved by using certain extractable agents, or combinations of extractable agents, as described in more detail below.

The containers, system components and systems of the invention can comprise or be made of a plastic material including at least one non-phthalate extractable agent. More particularly, the containers, system components and systems typically comprise or are made of a plastic material such as (but not limited to) PVC, and at least one extractable agent that is or includes a terephthalate ester, cyclohexane dicarboxylic acid ester, citrate ester, or polyol ester. The at least one extractable agent can be present in an amount or in amounts effective to reduce the brittleness of the PVC polymer.

The present inventors have found that surprisingly, considerable amounts of DEHP and phthalates in general leach not only during the storage of blood components, but already during the initial collection and processing steps. Also, DEHP and phthalate contamination may occur even after storage, during transfusion with systems that comprise DEHP or other phthalates. Moreover, it was demonstrated that a considerable reduction in the DEHP content of stored blood component products could be achieved when not only the container walls, but also additional container components, such as injection molded components and tube inserts, were made DEHP-free or phthalate-free.

Thus, it now has been found that the quality of blood and blood components can be significantly improved if the entire system, system components and containers used for the collection, processing, storage and transfusion of blood and/or blood components are essentially or entirely DEHP-free or, more preferably, are essentially or entirely phthalate-free.

Moreover, it has been found that the quality of blood component products can be enhanced by using certain combinations of extractable agents, or using certain combinations of extractable agents and additive solutions.

DEFINITIONS

The expression "about" as used herein is intended to signify a range of ±10% or less, preferably of ±5% or less, of a given value.

The expression "phthalate" as used herein means "ortho-phthalate", and thus designates the salts of ortho-phtalic acid. It is also intended to encompass ortho-phtalic acid (benzene-1,2-dicarboxylic acid) as such, as well as the esters of ortho-phthalic acid.

As used herein, the term "extractable agent" includes extractable plasticizers. The term may include agents that act as plasticizers for some materials (e.g., PVC), but do not necessarily act as plasticizers relative to other materials.

"w/w", as used herein, means "weight/weight" or "weight by weight".

"DEHP-free" as used herein can mean "produced without use of DEHP", or "not containing any DEHP".

"Phthalate-free" as used herein can mean "produced without use of phthalate", or "not comprising any phthalate".

Further definitions are provided in the detailed description throughout, as required.

Containers

According to a first aspect, the invention provides for containers for blood or a blood component.

The containers can be storage containers, or can be transit containers, such as collection or processing containers. The containers can be suitable for the storage or transit of whole blood and/or blood components such as RBC, plasma and platelets. The containers may be gas-permeable for oxygen and carbon dioxide.

It is understood that the containers described herein can be used in the blood component products, systems and methods according to the invention.

Preferably, the containers comprise or are made of polymeric material(s). PCV is a preferred polymeric material.

The containers include one or more container walls which define an interior chamber for receiving blood or a blood component. The walls can comprise or consist of polymeric material(s). The container walls can comprise or can be sheets comprising or consisting of polymeric material(s).

By way of example, two container walls can be brought together and sealed along their peripheries to form a container using methods known in the art, such as, but not limited to, high-frequency sealing. Other ways of making a container are known to those of skill in the art and are within the scope of the present disclosure.

Accordingly, a container for blood or a blood component is provided, the container comprising one or more container walls defining an interior chamber. The container walls can comprise one or more layers, the layers consisting of a composition comprising one or more polymeric materials, PCV being a preferred polymeric material, and at least one extractable agent. The extractable agent is selected from the group consisting of a terephthalate ester, a cyclohexane dicarboxylic acid ester, a citrate ester, and a polyol ester.

Preferably, the container further comprises one or more additional components besides the container wall(s) defining the interior chamber. An "additional component" as used herein can mean a component of the container that is not a container wall. The additional component(s) can be injection molded, extruded or calandered. The component(s) can be selected from the group consisting of an outlet port (preferably a spike port), an inlet port (preferably a tube insert or breaker port), an adapter, a spike, a seal, a valve, a tube, and a label (preferably a primary blood bag label), and combinations thereof.

The container may comprise still further components, as required.

Importantly, the container comprises about 3% or less than about 3% (w/w) of di-2-ethylhexyl phthalate (DEHP). For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

Preferably, the container comprises less than about 3% (w/w) of phthalates. For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

More preferably, the container is DEHP-free. Most preferably, the container is phthalate-free.

As indicated above, the container comprises one or more container walls. Thus, the container can comprise at least one, at least two, at least three, at least four, five or even more than five container walls, such as one, two, three, four, or five container walls. In embodiments with more than one container walls, such as two container walls, the container walls can be the same, or can be different from each other. Preferably, the container walls are the same.

The one or more walls can define an interior chamber adapted for being filled with liquids, such as blood, blood components and additive solutions. The walls can be or can comprise sheets. The walls can have an inner and an outer surface, wherein the inner surface is in closer proximity to the interior chamber than the outer surface. The inner surface may be in contact with a content of the interior chamber, such as blood, a blood component, and/or an additive solution. The outer surface may be formed by a first layer and the inner surface may be formed by a second layer, or vice versa.

By way of example only, containers of the type described herein may have a container wall or sheet thickness of between approximately 0.1 to 1.0 mm. They may include a non-smooth or any surface finish that minimizes sheet sticking and also influence the final contact surface. Typically, containers of the type described herein may have a container volume (i.e., interior chamber volume) of approximately 150 ml to 4 liters. The containers are preferably sterilizable by autoclaving and such autoclavable containers may typically have a 65-90 durometer (Shore A scale).

It is preferred that one or more, preferably all container walls comprise about 3% or less than about 3% (w/w) of DEHP. For example, one or more, preferably all container walls comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

More preferably, one or more, preferably all container walls, comprise about 3% or less than about 3% (w/w) of phthalates For example, one or more, preferably all container walls comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

Even more preferably, the one or more container walls are DEHP-free. Most preferably, the one or more container walls are phthalate-free.

Each of the one or more container walls independently can comprise or consist of one or more layers, such as at least 2, at least 3, at least 4, at least 5, at least 7 or at least 8 layers, for example 1, 2, 3, 4, 5, 6, 7, or 8 layers. 1, 2 or 3 layers are preferred. The layers may be foils or sheets. The layers may be produced by extrusion.

Each layer independently comprises or consists of a composition comprising or consisting of one or more polymeric materials and at least one extractable agent.

Compositions comprised in or making up for the layer are now described in more detail. It should be noted however that the compositions can also be used, without limitation, for additional container components and system components of the invention.

The composition comprises or consists of one or more polymeric materials and at least one extractable agent. PCV is a preferred polymeric material.

The extractable agent is selected from the group consisting of a terephthalate ester, a cyclohexane dicarboxylic acid ester, a citrate ester, and a polyol ester. A preferred extractable is a terephtalate ester. A cyclohexane dicarboxylic acid ester is likewise preferred.

A preferred example of a terephthalate ester is di-2-ethyl hexyl terephthalate (DEHT). DEHT is commercially available from e.g. Eastman Chemical Co. (Kingsport, Tenn., USA; product name Eastman 168).

A preferred example of a cyclohexane dicarboxylic acid ester is 1,2-cyclohexane dicarboxylic acid diisononyl ester (DINCH). DINCH is commercially available from available from e.g. BASF (Ludwigshafen, Germany; product name Hexamoll™). Another example of a cyclohexane dicarboxylic acid ester is 1,2-cyclohexyl dicarboxylic acid di-2-ethylhexyl ester (DEHCH).

Preferred examples of citrate esters comprise acetyl tributyl citrate (ATBC), acetyl trihexyl citrate (ATHC), and butiryl trihexyl citrate (BTHC), ATBC and BTHC being most preferred. These citrate esters are available from e.g. Vertellus Specialties Inc (Parsippany, N.J., USA; product names Citroflex® A4, A6, or B6).

A preferred example of a polyol ester is pentaerythritol tetravalerate, available from e.g. Perstorp (Perstorp, Sweden, product name Pevalen™).

Accordingly, the at least one extractable agent that is selected from the group consisting of a terephthalate ester, a cyclohexane dicarboxylic acid ester, a citrate ester, and a polyol ester can preferably be at least one extractable agent selected from the group consisting of DEHT, DINCH, DEHCH, ATBC, ATHC, BTHC and pentaerythritol tetravalerate. The at least one extractable agent that is selected from this group may extract to a level of more than one tenth, preferably more than one fifth of the extraction level of DEHP in that same medium.

Preferably, the composition comprises at least two, or at least three extractable agents selected from the group consisting of a terephthalate ester, a cyclohexane dicarboxylic acid ester, a citrate ester, and a polyol ester, such as at least two, or at least three extractable agents selected from the group consisting of DEHT, DINCH, DEHCH, ATBC, ATHC, BTHC and pentaerythritol tetravalerate. The combined effort of these plasticizers may extract to a level of more than one fifth of, preferably a level similar to, the extraction level of DEHP in that same medium. The extraction level of the individual plasticizers within the combined effort of these plasticizers may be more than one fifth/tenth, preferably more than one third, of the extraction level of DEHP in that same medium in ratio to the comparative presence of that individual plasticizer in PVC polymer. The extraction level of the individual plasticizer within the combined effort of plasticizers is not necessarily in ratio to the extraction level of that plasticizer when employed as a one extractable agent in that same medium. Preferred combinations of extractable agents are described in more detail below.

In addition to the at least one, at least two, or at least three extractable agents, the composition may comprise non-extractable plasticizers such as tris (2-ethylhexyl) trimellitate (TOTM), epoxidised soybean oil (ESO) and/or epoxidised linseed oil (ELO) as desired. ESO and ELO are able to graft to the PVC, when the PVC is thermally degraded, so also function as a heat stabilizer. Non-extractable plasticizers are plasticizers that extract at a rate of one tenth or less in a fluid media of the rate DEHP would extract from PVC into the same media.

It is known to the person skilled in the art that the level of extraction in certain media depends on the type of medium employed, in addition to the final surface contact area and duration and temperature of contact between the polymer and the extraction medium and the final ratio of PVC and extractable agent in the PVC.

According to some embodiments, the composition does not comprise any extractable agents or non-extractable plasticizers in addition to the one or more extractable agents selected from the group consisting of a terephthalate ester, a cyclohexane dicarboxylic acid ester, a citrate ester, and a polyol ester, or does not comprise any extractable agents in addition to the one or more extractable agents selected from the group consisting of DEHT, DINCH, DEHCH, ATBC, ATHC, BTHC and pentaerythritol tetravalerate.

Preferred combinations of extractable agents, and combinations of extractable agents with non-extractable plasticizers such as TOTM are described in more detail below.

In all embodiments of the present invention, it preferred that the compositions comprise about or less than about 3% (w/w) of DEHP, such as about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

More preferably, the compositions comprise about 3% or less than about 3% (w/w) of phthalates, such as about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

Even more preferably, the compositions are DEHP-free. Most preferably, the compositions are phthalate-free.

The composition comprises one or more polymeric materials. For example, the composition can comprise at least two, at least three, at least four or at least five polymeric materials, such as 1, 2, 3, 4, or 5 polymeric materials. A composition comprising one or two polymeric materials is preferred; a composition comprising one polymeric material is even more preferred.

PVC is a highly preferred polymeric material for use in the present invention. Accordingly, it is highly preferred that the composition comprises PVC as a polymeric material. Even more preferably, the composition comprises one polymeric material only, the one polymeric material being PVC.

Thus, preferably, one or more than one, such as all, of the layers of a container comprise or consist of a composition comprising PVC as polymeric material, or as the only polymeric material, and at least one extractable agent as further described herein.

Alternatively, the polymeric material may be one or more non-PVC polyolefin homopolymers, co-polymers or blends thereof. Examples of suitable non-PVC polyolefins include polypropylene, polyethylene, including ultra-low density polyethylene (ULDPE) and very low density polyethylene (VLDPE). Biofine® (Fresenius Medical Care AG & Co. KGaA, Bad Homburg, Germany) is one suitable polymer comprising polyolefines. Other suitable materials include ethylene vinylacetate (EVA) and block co-polymers such as styrenic block copolymers comprising polystyrene blocks and rubber blocks. The rubber blocks may comprise polybutadiene, polyisoprene or their hydrogenated equivalents. Exemplary block co-polymers are Kraton® polymers (Kraton Polymers LLC). Exemplary formulations and/or polyolefins, polyolefin blends or other polymeric materials which are useful, either alone or in combination, in the manufacture of containers suitable for use in blood component products of the present disclosure are described in U.S. Pat. Nos. 5,026,347, 4,140,162, 5,849,843, and 6,579,583, all of which are incorporated herein by reference in their entireties. Of course, it will be appreciated that even in containers where the walls are made without any PVC, some PVC may be present in small amounts in the container as a whole.

A container wall may comprise or consist of at least one layer. The one layer may in whole or at least in part be made of or comprise a composition that includes one or more polymeric materials and at least one extractable agent that is or includes a terephthalate ester, cyclohexane dicarboxylic acid ester, citrate ester, or polyol ester in an amount effective to suppress hemolysis in RBCs and to still maintain the structural integrity and biocompatibility of the container during manufacture, sterilization and use.

The one or more polymeric materials of the composition may be blended together with the extractable agent or agents. The blend may further comprise non-extractable plasticizers such as TOTM, ESO and/or ELO. The composition preferably comprises 10% (w/w) or less (such as 8% or less, 5% or less, 3% or less, or 1% or less (w/w)) of TOTM. The composition preferably comprises 10% (w/w) or less (such as 8% or less, 5% or less, 3% or less, or 1% or less (w/w)) of ESO, of ELO, or of ESO and ELO.

In forming a multi-layer sheet, co-extrusion or lamination may be used. The blend may be formed into flat layers or sheets that are sealed together for example by lamination, solvents, heat, or high frequency sealing. If forming a container out of two or more sheets, heat or high-frequency sealing is preferably used, of which high-frequency sealing is most preferred.

If a container wall comprises or consists of more than one layer, the layers can be the same, or can be different from each other. For example, the layers may vary in thickness, composition, or both. In particular, different layers comprised in a container wall may differ from each other regarding the polymeric materials(s) and/or extractable agent comprised in each layer. Thus, in aspects where the container walls comprise more than one extractable agent, the different extractable agents may be comprised in the same, or in different layers of the container wall.

To give a non-limiting example, a container wall may be made of more than one layer, provided for example as a layer laminate, wherein the layers comprise or are made of different compositions. The compositions may differ in the at least one extractable agent selected from the group consisting of a terephthalate ester, cyclohexane dicarboxylic acid ester, citrate ester, or polyol ester comprised. Albeit the compositions may also differ in the polymeric material, it is preferred that PVC is used as polymeric material in all compositions.

A preferred composition comprises PVC and at least one extractable agent selected from the group consisting of a terephthalate ester, a cyclohexane dicarboxylic acid ester, a citrate ester, and a polyol ester in an amount effective to reduce the rigidity of the polymer. More specifically, a preferred composition incorporates one, two, three or more of the disclosed extractable agents in amounts sufficient to suppress hemolysis of red blood cells, allow for the storage of frozen plasma, and provide good gas permeability for the storage of platelets.

Accordingly, the composition may include about 20% to about 45% (w/w) of the at least one extractable agent, such as about 25% to about 40% (w/w), or about 30% to about 35% (w/w). If the composition comprises more than one extractable agent selected from the group consisting of a terephthalate ester, a cyclohexane dicarboxylic acid ester, a citrate ester, and a polyol ester, all of these extractable agents taken in combination may account for about 20% to about 45% (w/w) of the composition, such as for about 25% to about 40% (w/w), or for about 30% to about 35% (w/w).

According to some embodiments, each of the extractable agents accounts for at least about 5% (w/w) of the extractable agent.

The remainder of the composition may be made up of one or more polymeric material such as PVC, and optionally non-extractable plasticizers, stabilizers and/or lubricants. The composition may comprise about 80% to about 45% (w/w), such as about 75% to about 50% (w/w), preferably about 70% to about 55% (w/w) or about 65% to about 60% (w/w) of PVC and optionally non-extractable plasticizers, stabilizers, co-stabilizers and lubricants.

For example, TOTM is a non-extractable plasticizer. TOTM may be comprised in an amount making up for up to about 25% w/w of the total weight of extractable agents and non-extractable plasticizers comprised (such as up to 5, 10, 15 or 20% w/w). TOTM may make up for up to about 10% w/w (such as up to 1, 3, 5 or 8% w/w) of the composition.

An example of a co-stabilizer is epoxidized soy bean or linseed oil (ESO and ELO, respectively). The composition can comprise ESO and/or ELO in an amount making up for up to 10% w/w (such as up to 1, 3, 5, 8 or less than 10% w/w) of the composition. Co-stabilizers other than epoxidized oils may also be used. An example of a stabilizer is metal stearate, usually zinc octanoate or zinc stearate and calcium octanoate or calcium stearate (as such covered in Eur. Pharm.). Other non-toxic stabilizers may also be used. The stabilizer can be a stabilizer disclosed in Folarin, O. M., and Sadiku E. R. "Thermal stabilizers for poly (vinyl chloride): A review." (Int. J. Phys. Sci 6 (2011): 4323-4330; incorporated by reference in its entirety herewith).

In a non-limiting example, compositions described herein may include about 3.0% (w/w) or more than about 3.0% (w/w) of a stabilizer such as epoxidized oil and about 1.0% (w/w) or less than about 1.0% of a co-stabilizer such as metal stearate.

By way of example, the composition may comprise a polymeric material such as PVC and at least two extractable agents, such as those disclosed, but may have a molecular weight of between approximately 350 to 600 g/mol. Thus, at least two extractable agents may be combined with the base polymeric material (e.g., PVC) in one embodiment of the composition of the present disclosure.

While the use of layers or container walls comprising one extractable agent selected from the group consisting of a terephthalate ester, a cyclohexane dicarboxylic acid ester, a citrate ester, and a polyol ester has been found to yield good results, in particular for the use in transient containers, the use of more than one extractable agent selected from the group consisting of a terephthalate ester, a cyclohexane dicarboxylic acid ester, a citrate ester, and a polyol ester offers certain advantages, and specific combinations of extractable agents selected from the above group are particularly preferred.

Accordingly, the present invention provides containers and container walls, the container or container walls comprising at least a second extractable agent that preferably is selected from the group consisting of a terephthalate ester, a cyclohexane dicarboxylic acid ester, a citrate ester, and a polyol ester. The at least one or first extractable agent and the second extractable agent can be comprised in the same layer, or can be comprised in different layers. Typically, the first and second extractable agents are different from one another.

Specifically, the composition of the one or more layers can comprise a second extractable agent, preferably a second extractable agent selected from the group consisting of a terephthalate ester, a cyclohexane dicarboxylic acid ester, a citrate ester, and a polyol ester. In this case, the second extractable agent is comprised in the same layer as the at least one or first extractable agent.

In the alternative, the container wall may comprise at least two layers, each of the layers comprising a composition comprising at least one extractable agent selected from the group consisting of a terephthalate ester, a cyclohexane dicarboxylic acid ester, a citrate ester, and a polyol ester, wherein one of the layers comprises a first extractable agent and another layer comprises a second extractable agent, the first and second extractable agents being different from one another.

Thus, the present invention provides for a container comprising one or more container walls, at least one of the container walls comprising a first layer and a second layer, wherein the first layer consists of a composition comprising one or more polymeric materials and at least one extractable agent selected from the group consisting of a terephthalate ester, a cyclohexane dicarboxylic acid ester, a citrate ester, and a polyol ester, wherein the second layer consists of a composition comprising one or more polymeric materials and at least one extractable agent selected from the group consisting of a terephthalate ester, a cyclohexane dicarboxylic acid ester, a citrate ester, and a polyol ester, wherein the extractable agents comprised in the composition of the first and second layers are the same, or are different from each other. The container walls may comprise additional layers.

The container wall(s) can be made of a composition that includes a polymeric material and at least a first extractable agent selected from the group consisting of a terephthalate ester, a cyclohexane dicarboxylic acid ester, a citrate ester, and a polyol ester, and can further include a second extractable agent. The extractable agent can be selected from the group consisting of a terephthalate ester, a cyclohexane dicarboxylic acid ester, a citrate ester, and a polyol ester. The second extractable agent can be comprised in the same layer as the first extractable agent, or in a different layer.

Also, present invention provides containers and container walls, the container or container walls comprising at least a third extractable agent that preferably is selected from the group consisting of a terephthalate ester, a cyclohexane dicarboxylic acid ester, a citrate ester, and a polyol ester.

The at least one or first extractable agent, the second extractable agent, and the third extractable agent can be comprised in the same layer, or can be comprised in different layers. Typically, the first and second and third extractable agents are different from one another.

In other words, if the container wall comprises more than one layer, the compositions of the layers may vary in the one or more extractable agents comprised.

While it is understood that in embodiments of the invention where at least two, or at least three extractable agents are used, these can be comprised in different walls or layers, the at least two, or at least three extractable agents can more preferably and conveniently be comprised within the same composition and layer.

It has been observed that non-DEHP alternative plasticizers may not be as compatible with PVC, making it more difficult to produce materials that conform to the requirements of flexibility and strength set by blood banking. In addition, producing seals by solvents, heat, or high-frequency sealing may be more challenging.

The present inventors have found that certain extractable agents and combinations thereof are particularly useful to overcome limitations that may occur when DEHP/phthalates are omitted.

Particularly useful extractable agents according to the invention are extractable agents selected from the group consisting of DEHT, DINCH, DEHCH, ATBC, ATHC, BTHC and pentaerythritol tetravalerate, or combinations thereof. DEHT is preferred, DINCH is also preferred.

In the following, several particularly useful combinations are described. While these combinations are described in relation with the composition of the container, the description also applies for the system components, systems and blood component products of the present invention.

At least two extractable agents of the particularly useful combinations can be provided within a container wall within the same layer, or within different layers. As described above, the at least two extractable agents can conveniently be comprised within the same composition.

For example, one extractable agent can be a cyclohexane dicarboxylic acid ester and one extractable agent can be selected from the group consisting of a citrate ester, a terephthalate ester and a polyol ester. Accordingly, the invention provides for DINCH as a first non-extractable agent and a second extractable agent selected from the group consisting of DEHT, BTHC; ATBC and pentaerythritol tetravalerate.

Also, one extractable agent can be a terephthalate ester and one extractable agent can be selected from the group consisting of a citrate ester, a cyclohexane dicarboxylic acid ester and a polyol ester. Accordingly, the invention provides for DEHT as a first non-extractable agent and a second extractable agent selected from the group consisting of DINCH, BTHC; ATBC and pentaerythritol tetravalerate.

A combination of a cyclohexane dicarboxylic acid ester with one or more citrate esters, terephthalate esters or polyol esters has been found very useful. Without wishing to be bound by theory, it was found that when these extractable agents are used in combination, the cyclohexane dicarboxylic acid ester facilitates the homogenous introduction of the one or more citrate esters in the PVC structure. The effect was particularly pronounced when a combination of DINCH with ATBC and/or BTHC was used. Moreover, a combination of DINCH with ATBC and/or BTHC was found to suppress hemolysis of RBCs superior to the use of DINCH, ATBC or BTHC alone, and in a more than additive manner. This beneficial effect was also observed when DINCH, ATBC and/or BTHC were provided in different layers. A combination of DINCH and BTHC was also found to synergistically interact to improve gas permeability of the polymeric material, which is highly desirable for a broad range of applications. Accordingly, the cyclohexane dicarboxylic acid ester can be DINCH and the citrate ester can be ATBC. The cyclohexane dicarboxylic acid ester can be DINCH and the citrate ester can be BTHC. A more than additive effect on gas permeability can also observed when DINCH is combined with and pentaerythritol tetravalerate.

The advantageous effects of a combination of DINCH with ATBC were observed over a wide range of DINCH to ATBC ratios, however were most pronounced when DINCH makes up for about 70% to about 90%, preferably about 75% to about 85%, more preferably about 80% (w/w) of the total weight of DINCH and ATBC, and ATBC makes up for about 30% to about 10%, preferably about 25% to about 15%, more preferably about 20% (w/w).

For a combination of DINCH with BTHC, the advantageous effects were also observed over a wide range of DINCH to BTHC ratios, however were most pronounced when DINCH makes up for about 40% to about 60%, preferably about 45% to about 55%, more preferably about 50% (w/w) of the total weight of DINCH and BTHC, and BTHC makes up for about 60% to about 40%, preferably about 55% to about 45%, more preferably about 50% (w/w).

Also combinations of DINCH and pentaerythritol tetravalerate were found useful for a range of ratios, however particularly good results were obtained when DINCH makes up for about 40% to about 60%, preferably about 45% to about 55%, more preferably about 50% (w/w) of the total weight of DINCH and pentaerythritol tetravalerate, and pentaerythritol tetravalerate makes up for about 60% to about 40%, preferably about 55% to about 45%, more preferably about 50% (w/w).

Likewise, a combination of a cyclohexane dicarboxylic acid ester with a terephthalate ester was found to be very useful. This applies in particular to combinations of DINCH and DEHT. Again, without wishing to be bound by theory, it was found that this combination of extractable agents showed an advantageous effect on material viscosity and curing during processing. Of note, this beneficial effect was also observed when combining DINCH and BTHC or ATBC. Foil extendibility was significantly improved for all of these combinations (i.e. curing without PVC degradation was facilitated). Also, the combination of DINCH and DEHT was found to suppress hemolysis of RBCs superior to the use of DINCH or DEHT alone, and in a more than additive manner. This beneficial effect was also observed when DINCH and DEHT were provided in different layers.

Here, the advantageous effects of a combination of DINCH with DEHT were also observed over a wide range of DINCH to DEHT ratios, however were most pronounced when DINCH makes up for about 50% to about 70%, preferably about 55% to about 65%, more preferably about 60% (w/w) of the total weight of DINCH and DEHT, and DEHT makes up for about 30% to about 50%, preferably about 35% to about 45%, more preferably about 40% (w/w).

Combinations of DEHT with ATBC and of DEHT with BTHC have also been found useful, for example when DEHT makes up for about 50% to about 70%, preferably about 55% to about 65%, more preferably about 60% (w/w) of the total weight of DEHT and ATBC, and ATBC makes up for about 30% to about 50%, preferably about 35% to about 45%, more preferably about 40% (w/w), or when DEHT makes up for about 40% to about 60%, preferably about 45% to about 55%, more preferably about 50% (w/w) of the total weight of DEHT and BTHC, and BTHC makes up for about 60% to about 40%, preferably about 55% to about 45%, more preferably about 50% (w/w).

Combinations of DEHT and pentaerythritol tetravalerate were found useful as well, for a range of ratios, however particularly good results were obtained when DEHT makes up for about 40% to about 60%, preferably about 45% to about 55%, more preferably about 50% (w/w) of the total weight of DEHT and pentaerythritol tetravalerate, and pentaerythritol tetravalerate makes up for about 60% to about 40%, preferably about 55% to about 45%, more preferably about 50% (w/w).

ATBC can be used in combination with DEHT or DINCH; as described above. However, for some applications, for example for containers intended for the collection of whole blood and subsequent centrifugation, combinations of ATBC with one of the other extractable agents, such as BTHC or pentaerythritol tetravalerate are also very preferred.

With all of these advantageous combinations, the use of PVC as polymeric material is preferred.

As indicated above, the container comprises preferably one or more additional components besides the one or more container walls. The component may be any component typically comprised in a container for blood or blood component products. The container may comprise still further components, as required.

The inventors have found that leaching of DEHP or phthalates during handling does not only result from contact with large contact surfaces, such as container wall surfaces. Rather, further components comprised in the container can also contribute significantly to the observed leaching.

Thus, the container of the present invention as a whole, without focusing on the container walls only, is adapted so as to minimize DEHP or phthalate leaching. Accordingly, the container comprises only about 3% or less of DEHP, as detailed above. Preferably, the container comprises less than about 3% (w/w) of phthalates, as detailed above.

The one or more additional components comprised in the container can be selected from the group consisting of an outlet port (preferably a spike port), an inlet port (preferably a tube insert or breaker port), an adapter, a spike, a seal, a valve, a tube, and a label (preferably a primary blood bag label), and combinations thereof.

The one or more additional components comprised in the container may be injection molded components. Injection-molded components usually are of complex drawing and include temper-proof membranes or other parts. A negative mould of these parts is usually made of stainless steel, and under regulated temperature and pressure (for regulated flow of the PVC and limitation of burn pits and overall discoloration) the PVC is injected in the mold, then left to cool.

The one or more additional components comprised in the container may be extruded components, such as tubes, label material or both. Label material may also be calandered.

Tubes can be of soft PVC. Labels may be of a different material, but either a porous or polar surface material to allow for the incorporation of ink. If any plasticizer is used for the label material, this does not need to be an extractable agent, however this should not limit the printability of the PVC. So, it can be any plasticizer (e.g. including TOTM). An example of a non-PVC label material is Teslin material, available from Baxter.

For example, the container may comprise one or more ports for connection with a tubing, docking devices or the like to establish flow into and out from the interior chamber of the container.

The one or more additional components may comprise or consist of a composition comprising one or more polymeric materials and at least one extractable agent selected from the group consisting of a terephthalate ester, a cyclohexane dicarboxylic acid ester, a citrate ester, and a polyol ester.

The composition can, without limitation, be a composition as described above for the composition of the layers of the container wall. It should however be noted that the composition of the container wall(s) and the one or more additional components can be chosen independently from each other. However, PVC is a highly preferred polymeric material also for the composition of the one or more additional components.

Accordingly, the additional component may comprise or consists of a composition comprising PVC, preferably wherein the composition comprises one polymeric material, the one polymeric material being PVC.

Alternative materials that have been described above in relation with the container walls are, in principle, also suitable for the use in the one or more additional container component.

As already described above for the composition in relation with the container layers, the composition of the additional component may comprise a second extractable agent, preferably a second extractable agent selected from the group consisting of a terephthalate ester, a cyclohexane dicarboxylic acid ester, a citrate ester, and a polyol ester. The composition may further comprise a third extractable agent, preferably a third extractable agent selected from the group consisting of a terephthalate ester, a cyclohexane dicarboxylic acid ester, a citrate ester, and a polyol ester.

Examples of extractable agents, preferred extractable agents and preferred combinations of extractable agents have already been described above in relation with the compositions comprised in the layers of the container walls, and apply, without limitation, also for the additional container component.

Moreover, the inventors have found that a combination of DINCH and DEHT in relation with injection molded components offers the further advantage that they complement each other in terms of viscosity. During injection molding the material typically is run through devices under high temperatures. A too viscous compound may result in strain in the components afterwards. A less viscous compound may relieve the strain, but there a low shore A formulation may become impossible. The combination of DINCH and DEHT was found to relieve the strain, but at the same time allow for a formulation exhibiting a comparably low shore A.

Accordingly, of the combinations of extractable agents described above for the compositions comprised in the layers of the container walls, a combination of DINCH and DEHT is highly preferred for the composition of the additional container component.

Also, for injection-molded additional components, a combination of DINCH and ATBC is even more highly preferred.

For additional components that are tubes, a combination of DEHT and ATBC is even more highly preferred.

It is highly preferred that one or more that one, preferably all additional container components comprise about 3% or less than about 3% (w/w) of DEHP. For example, the additional container component comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

Preferably, the additional container component comprises about 3%, or less than about 3% (w/w) of phthalates For example, the additional container component comprises about 2.5% (w/w) or less, about 2% (w/w) or less, about 1.5% (w/w) or less, about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

More preferably, the additional container component is DEHP-free. Most preferably, the additional container component is phthalate-free.

As already explained above for the compositions comprised in the layers of the container walls, also for the additional container component compositions may comprise additional non-extractable plasticizers such as TOTM, ESO and/or ELO, as desired. The composition preferably comprises 10% (w/w) or less (such as 8% or less, 5% or less, 3% or less, or 1% or less (w/w)) of TOTM. The composition preferably comprises 10% (w/w) or less (such as 8% or less, 5% or less, 3% or less, or 1% or less (w/w)) of ESO, of ELO, or of ESO and ELO.

Also, the container as a whole may comprise one or more components (for example injection molded components) that comprise non-phthalate plasticizers such as TOTM, ESO and/or ELO, as desired. For example, these components may comprise 10% (w/w) or less (such as 8% or less, 5% or less, 3% or less, or 1% or less (w/w)) of TOTM. For example, the components may comprise 10% (w/w) or less (such as 8% or less, 5% or less, 3% or less, or 1% or less (w/w)) of ESO, of ELO, or of ESO and ELO. The components may or may not comprise one or more extractable agents, as defined above, as long as the container has the low DEHP or phthalate content according to the invention. Preferably, these components are DEHP-free, or are phthalate-free.

System Components

The present inventors have found that not only the sheeting of containers used in relation with the collection, processing, storage and transfusion of blood or blood components contribute to the leaching of DEHP/phthalates into blood and blood components. It was found that also further system components that typically comprise DEHP/phthalates as extractable agent besides containers or container walls, such as e.g. tubing and spike ports, account for DEHP/phthalate accumulation in the blood or blood component product, even if exposure or pass-through times may be comparably short.

Accordingly, the present invention further provides for a system component. The system component is suitable or adapted for the use in a system for blood or blood component collection, processing, storage and/or transfusion.

The system component comprises or consists of a composition comprising one or more polymeric materials and at least one extractable agent selected from the group consisting of a terephthalate ester, a cyclohexane dicarboxylic acid ester, a citrate ester, and a polyol ester, and is characterized in that it comprises about 3% or less than about 3% (w/w) of DEHP, preferably wherein the system component comprises about 3% or less than about 3% (w/w) of phthalates.

For example, the system component comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% (w/w) or less, or about 0.0000% (w/w) of DEHP.

Preferably, the system component comprises about 3%, or less than about 3% (w/w) of phthalates For example, the system component comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

Even more preferably, the system component is DEHP-free. Most preferably, the system component is phthalate-free.

The composition of the system component may, without limitations, be a composition as described in detail above for the layer composition of the container wall. In particular, the above description relating to the one or more extractable agents and preferred combinations thereof applies, without limitation, also to the composition of the system component.

A preferred extractable agent may be terephtalate ester. A cyclohexane dicarboxylic acid ester is likewise preferred. A preferred example of a terephthalate ester is DEHT. A preferred example of a cyclohexane dicarboxylic acid ester is DINCH. Preferred examples of citrate esters comprise ATBC, ATHC, and BTHC, ATBC and BTHC being most preferred. A preferred example of a polyol ester is pentaerythritol tetravalerate.

Preferably, the system component may comprise or consist of a composition comprising polyvinylchloride (PVC). Preferably, the composition comprises one polymeric material, the one polymeric material being PVC.

The system component may be selected from the group consisting of an outlet port (preferably a spike port), an inlet port (preferably a tube insert or breaker port), an adapter, a spike, a seal, a valve, a tube, and a label (preferably a primary blood bag label), and combinations thereof.

The system component may be an injection molded system component, or may be an extruded system component. The system component may be calandered.

While system components comprising or consisting of a composition comprising one extractable agent selected from the group consisting of a terephthalate ester, a cyclohexane dicarboxylic acid ester, a citrate ester, and a polyol ester can advantageously reduce DEHP and phthalate leaching, the combination of two or more extractable agents may be advantageous, especially in embodiments where the polymeric material is or comprises PVC:

Accordingly, the system component or its composition can further comprise a second extractable agent, preferably a second extractable agent selected from the group consisting of a terephthalate ester, a cyclohexane dicarboxylic acid ester, a citrate ester, and a polyol ester.

The system component or its composition can further comprise a third extractable agent, preferably a third extractable agent selected from the group consisting of a terephthalate ester, a cyclohexane dicarboxylic acid ester, a citrate ester, and a polyol ester.

The present inventors have found that certain combinations of extractable agents are particularly useful to overcome limitations that may occur when DEHP/phthalates are omitted. With all of these advantageous combinations, the use of PVC as polymeric material is preferred.

For example, one extractable can be a cyclohexane dicarboxylic acid ester and one extractable agent is selected from the group consisting of a citrate ester, a terephthalate ester and a polyol ester. The cyclohexane dicarboxylic acid ester can be DINCH and the citrate ester can be ATBC. The cyclohexane dicarboxylic acid ester can be DINCH and the citrate ester can be BTHC. The cyclohexane dicarboxylic acid ester can be DINCH and the polyol ester can be pentaerythritol tetravalerate. The cyclohexane dicarboxylic acid ester can be DINCH and the terephthalate ester can be DEHT. Combinations of DEHT with ATBC, of DEHT with BTHC, and combinations of DEHT with pentaerythritol tetravalerate are also useful.

For example, a combination of a cyclohexane dicarboxylic acid ester with one or more citrate esters has been found very useful. As explained above, the citrate esters facilitate the homogenous introduction of the cyclohexane dicarboxylic acid ester in the PVC structure; also, the combination may result in a reduced volatility of the extractable agents. The effect was particularly pronounced when a combination of DINCH with ATBC and/or BTHC was used.

The advantageous effects of a combination of DINCH with ATBC were observed over a wide range of DINCH to ATBC ratios, however were most pronounced when DINCH makes up for about 70% to about 90%, preferably about 75% to about 85%, more preferably about 80% (w/w) of the total weight of DINCH and ATBC, and ATBC makes up for about 30% to about 10%, preferably about 25% to about 15%, more preferably about 20% (w/w).

For a combination of DINCH with BTHC, the advantageous effects were also observed over a wide range of DINCH to BTHC ratios, however were most pronounced when DINCH makes up for about 40% to about 60%, preferably about 45% to about 55%, more preferably about 50% (w/w) of the total weight of DINCH and BTHC, and BTHC makes up for about 60% to about 40%, preferably about 55% to about 45%, more preferably about 50% (w/w).

Also combinations of DINCH and pentaerythritol tetravalerate were found useful for a range of ratios, however particularly good results were obtained when DINCH makes up for about 40% to about 60%, preferably about 45% to about 55%, more preferably about 50% (w/w) of the total weight of DINCH and pentaerythritol tetravalerate, and pentaerythritol tetravalerate makes up for about 60% to about 40%, preferably about 55% to about 45%, more preferably about 50% (w/w).

Combinations of DEHT and ATBC have also been found useful, e.g. when DEHT makes up for about 50% to about 70%, preferably about 55% to about 65%, more preferably about 6" (w/w) of the total weight of DEHT and ATBC, and ATBC makes up for about 30% to about 50%, preferably about 35% to about 45%, more preferably about 40% (w/w).

Combinations of DEHT and BTHC have also been found useful, e.g. when DEHT makes up for about 40% to about 60%, preferably about 45% to about 55%, more preferably about 50% (w/w) of the total weight of DEHT and BTHC, and BTHC makes up for about 60% to about 40%, preferably about 55% to about 45%, more preferably about 50% (w/w).

Combinations of DEHT and pentaerythritol tetravalerate were found useful as well, for a range of ratios, however particularly good results were obtained when DEHT makes up for about 40% to about 60%, preferably about 45% to about 55%, more preferably about 50% (w/w) of the total weight of DEHT and pentaerythritol tetravalerate, and pentaerythritol tetravalerate makes up for about 60% to about 40%, preferably about 55% to about 45%, more preferably about 50% (w/w).

Moreover, for certain system components such as tubes, flexibility is important. Besides being flexible, tubes should be non-kinking, and desirably also high-frequency sealable and dockable with sterile closure. In general, the slowly-diffusing plasticizers or extractable agents DINCH and DEHT are less able to retain the flexibility of the tube for e.g. pump applications than DEHP. E.g. the citrate esters do meet this requirement. However, these, especially ATBC, may be more leaching upon transient contact with blood components. Thus, according to a preferred embodiment, a combination of DINCH and/or DEHT with one or more citrate esters is used. The combination may further include TOTM as an additional non-extractable plasticizer. Also, different plasticizers exert different fluidity responses of the PVC to HF energy. DINCH and the citrates as a plasticizer are of lower viscosity when having responded to the energies, DEHT is of higher viscosity, and more similar to DEHP. The combination of DINCH and/or DEHT with one or more citrate esters and optionally, TOTM is preferred for tubings, but may be also used for other system components.

A combination of a cyclohexane dicarboxylic acid ester with a terephthalate ester was found to be very useful, since it may advantageously affect material viscosity during processing. This applies in particular to combinations of DINCH and DEHT. The effect was most pronounced when DINCH makes up for about 50% to about 70%, preferably about 55% to about 65%, more preferably about 60% (w/w) of the total weight of DINCH and DEHT, and DEHT makes up for about 30% to about 50%, preferably about 35% to about 45%, more preferably about 40% (w/w).

For injection-molded system components, a combination of DINCH and ATBC is even more highly preferred.

For system components that are tubes, a combination of DEHT and ATBC is even more highly preferred.

As indicated above, the composition of the system component may comprise additional non-phthalate plasticizers such as TOTM, ESO and/or ELO, as desired. The composition preferably comprises 10% (w/w) or less (such as 8% or less, 5% or less, 3% or less, or 1% or less (w/w)) of TOTM. The composition preferably comprises 10% (w/w) or less (such as 8% or less, 5% or less, 3% or less, or 1% or less (w/w)) of ESO, of ELO, or of ESO and ELO.

Systems

In a further aspect, the present invention provides a system. The system is suitable or adapted for blood or blood component collection, processing, storage and/or transfusion. Preferably, the system allows for leukocyte reduction, e.g. by one or more leukocyte filters.

The system comprises at least one system component according to the invention as described herein. In the alternative or in addition, the system comprises at least one container according to the invention as described herein. The compositions and extractable agents or extractable agents combinations comprised therein can be chosen independently for the individual system components and containers comprised in the system according to the invention.

The system is characterized in that it comprises less than about 3% (w/w) of di-2-ethylhexyl phthalate, preferably wherein the system comprises less than about 3% (w/w) of phthalates.

For example, the system comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

For example, the system comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

Even more preferably, the system is DEHP-free. Most preferably, the system is phthalate-free.

It is also highly preferred that for the system, the system components and/or containers according to the invention taken individually, and the compositions comprising the one or more polymeric materials and at least one extractable agent comprised therein have the above-indicated low DEHP or phthalate content, or even more preferably, are DEHP-free or phthalate-free.

The structure and built of the system according to the invention can be as generally known in the art. However, the system is distinguished over the prior art systems by virtue of its low DEHP or phthalate content, or in that the system is even DEHP-free or phthalate-free. This can be achieved by using one or more system components and/or containers according to the present invention, which have been described in detail above.

It is understood that the system may comprise one or more components in addition to the system components and/or containers according to the present invention, as long as the overall DEHP or phthalate content is as indicated above.

For example, the system may comprise needles or other components that do not comprise polymeric materials, and hence do not encompass extractable agents or plasticizers at all. Also, the system may or may not comprise additive solutions and/or anticoagulants.

However, the system may also comprise further components that comprise polymeric materials. These components will typically comprise one or more extractable agents and/or non-extractable plasticizers, which may be different from those according to the present invention. Nevertheless, the system according to the invention may comprise one or more of these components, as long as the DEHP or phthalate content of the system does not exceed 3% (w/w), as detailed above. It is understood that most preferably, these components themselves exhibit the low DEHP or phthalate content not exceeding 3% (w/w), and most preferably are DEHP-free, or are phthalate-free. Examples of components sufficing these criteria are tubings or other components comprising TOTM as plasticizer. Accordingly, the system may comprise one or more components comprising non-phthalate plasticizers such as TOTM, ESO and/or ELO, as desired.

The system may be a system with or without in-line filtration for leukodepletion. It is however preferred that the system allows for leukocyte reduction (e.g. via filtration), in particular so as to provide leukocyte depleted red blood cells.

A system according to the invention may include a needle for donor venipuncture and a bacteria diversion pouch to collect a first volume of blood that contains skin from the puncture and skin bacteria. The system can be adapted to allow for the collection of blood in a first container or collection container, which may contain an anticoagulative agent, such as a calcium chelating agent to establish anticoagulation. Preferably, the resistance through the needle, collection tube and in the collection container is low enough to establish, with the diastolic pressure of the donor, the collection of 450-500 ml of blood within 12-15 minutes. Preferably, the amount of air is limited so that no air-induced hemolysis occurs. Preferable, no turbulence is induced so that no turbulence-induced hemolysis occurs. Preferably, the container inner surface is vast enough to collect up to 500 ml of blood without increase of the internal pressure, and preferably, no internal surface cleavage occurs. The container set may allow for manual or automated mixing during collection to ensure complete and immediate anticoagulation of the collected blood. Preferable, the tube and container surface does not initiate severe activation of the blood platelets and plasma coagulation factors.

The collection container may be connected to one or more processing and storage containers and/or filters via tubing. The container may comprise ports that are designed such that no blood flow occurs during collection, but blood flow may be established in a later stage. In such cases, ports may contain breakers or a compoflow breaker.

One of the containers that may be connected to the collection container, either directly or via an intermediate processing container, is the plasma storage container. This means that the materials used in the plasma container are compatible to and sealable with the materials of the collection or intermediate container. The plasma container allows for the collection of the plasma either via gravity or via automated processing machines such as the Compomat.

The collection container may further be connected to storage containers for red cell concentrate and platelets.

In the following, non-limiting exemplary systems according to the invention will be described.

FIG. 1 shows a non-limiting exemplary system according to the invention. The system comprises at least one container (14). The container (14) is a container according to the invention, and comprises container walls defining an interior chamber. Optionally, the container (14) comprises one or two outlet ports (4). The outlet ports may or may not be protected by tamper evident protectors (1) comprising a tear line (6). One or more outlet ports (4) may comprise a puncturable non-sealable closure (12). A label area (7) may be provided on the container surface. The container (14) optionally may comprise one or more eyelets (11) and/or slits (13). The container (14) is connected to a system component according to the invention, such as collection tube (5). Optionally, the collection tube (5) is further connected to a blood taking needle (9) via a needle hub (10). The needle (9) may or may not be covered by a tamper evident protection cap (8). The container (14) may further be connected to a further system component according to the invention, such as a transfer tube (2), the transfer tube (2) optionally providing for a closure means (3).

In one embodiment, the system is used for the collection of whole blood. The system includes a needle (9) for donor venipuncture. The system allows for sterile venipuncture. Blood can be collected in a container (14) containing a calcium chelating agent to establish anticoagulation. The resistance through the needle (9), collection tube (5) and in the collection container (14) is low enough to establish, with the diastolic pressure of the donor, the collection of blood within the time it takes for the blood to clot. Preferably, the amount of air is limited so that no air-induced hemolysis occurs. Preferably, no turbulence is induced so that no turbulence-induced hemolysis occurs. Preferably, the inner surface of the container (14) is vast enough to collect up to 500 ml of blood without increase of the internal pressure, and no internal surface cleavage occurs. Preferably, the surfaces of the tube (5) and container (14) do not initiate severe activation of the blood platelets and plasma coagulation factors. For example, the system allows for manual or automated mixing during collection to ensure complete and immediate anticoagulation of the collected blood.

Typical amounts of anticoagulant range between 63 and 70 ml but can be different based on the collection volume.

It is preferred that the needle (9) and collection tube (5) are separated from the container (14) after the procedure has been completed to protect donor, physician, patient, and the unit of blood. It is then preferred that the collection tube (5) and needle (9) can be separated without a risk for leakage or bacterial contamination. Preferably, the tube (5) is sealed via a heat seal, or even more preferably, when PVC is the major constituent of the tube (5), via the application of a high-frequency seal. In general, tubes (2), typically made of plasticized PVC, are used to transfer whole blood or blood components from one part of the system to another part of the system. Tubes (2) typically are connected to other components by means of solvents rather than glue. It is highly preferred that the connections meet ISO3826 requirements.

The container (14) preferably is flexible, such that it contains no volume other than the anticoagulant before collection, but is able to expand to allow for the collection of the desired volume. The tube (5) and container (14) can allow for the detection and inspection of the contents. If the container is also indicated for the transfusion of blood, the container can be fitted with spike ports and a protective (but removable) cap that allows for the spike port to remain sterile until puncture.

Just like the other bags in a blood processing system, the container (14) can be provided with a label, such as a label containing (ISBT) relevant information such as production date, expiray date, reference number, lot number etc and indications for proper handling. Container (14) can have tube and/or injection molded components on either its top and/or bottom side, as desired, depending on the processing procedure of the particular blood bank and/or separation procedures in place.

In a preferred embodiment, the collection tube (5) is fitted with a diversion path and a diversion pouch (21) to collect the first volume of blood that contains skin from the donor's puncture wound and skin bacteria. After diversion of a first sample the passage of blood can be re-directed to the container (14). The tube to the diversion pouch preferably is provided with an irreversible or non-re-openable pinch clamp to avoid any flow back to the collection tube (5) after having taken a blood sample.

It may be desired that the container (14) is not indicated for the direct transfusion of the volume, but is fitted with one or more additional port entries (15, 16) that connect the container (14) to processing (18) and storage containers (17, 20, 24, 25) and filters via tubing (2).

Ports (15, 16, 4) can be designed such that no blood flow occurs during collection, but blood flow may be established in a later stage. To that end, ports may contain bag break-off parts or a Compoflow closure device. Ports (15, 16, 4) in containers (14, 17, 18, 20, 23, 24, 25, 26), such as flexible containers, can be tubes or tube inserts and/or injection molded components, allowing for fluid flow into or out of the containers (14, 17, 18, 20, 23, 24, 25, 26). The injection molded components can have a closure device that disables the flow of blood components until needed. Opening of this closure device can be achieved manually or automatically. A feature typically comprised in addition on storage containers (17, 20, 24, 25) is one or more spike ports, representing outlet ports (4), used for transfusion purposes.

Where connectors are used, the connector may be a Y-piece.

Figure 2:
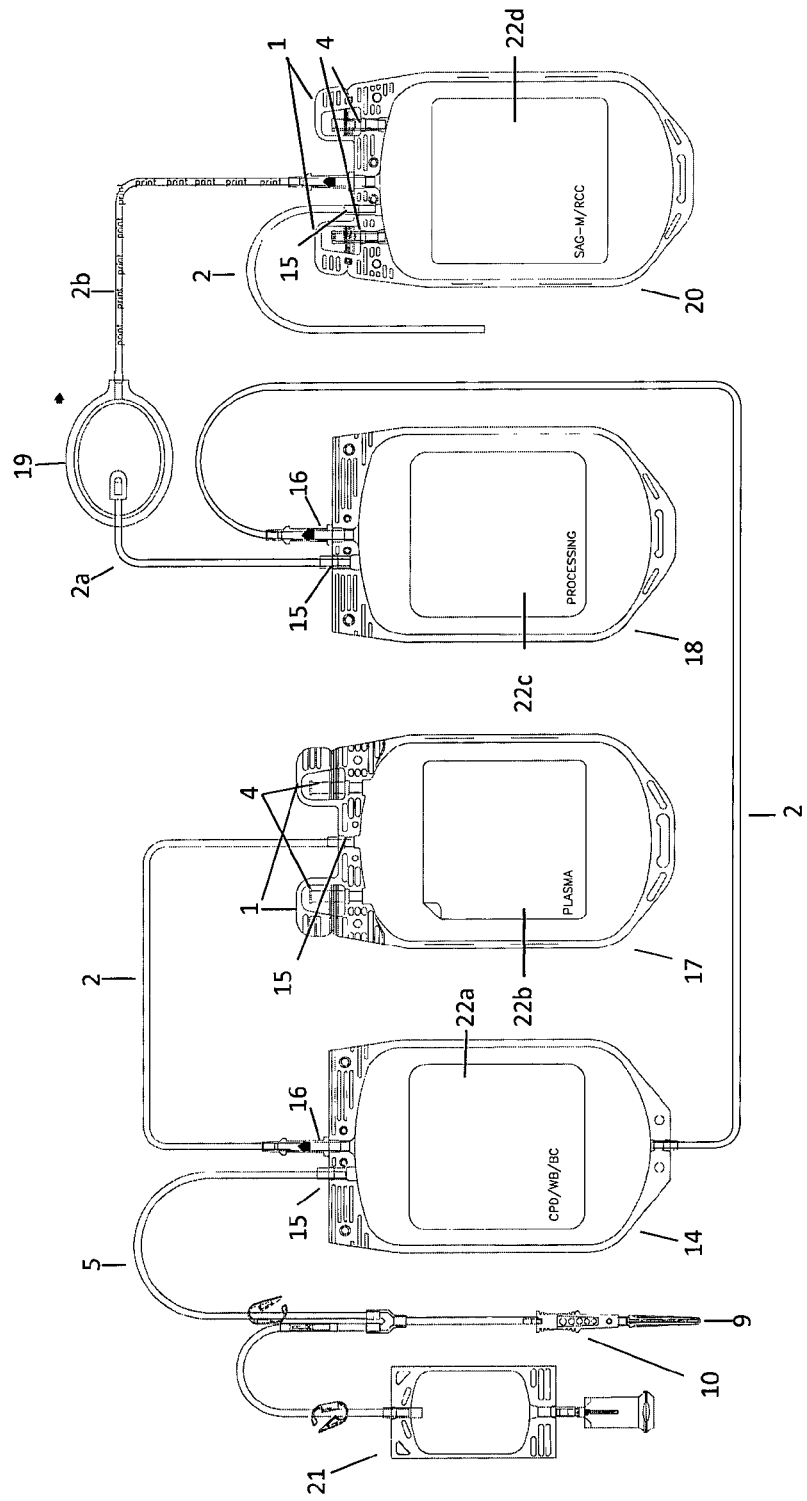
FIG. 2 shows an exemplary system according to the invention.

FIG. 2 shows a non-limiting exemplary system according to the invention, comprising containers and system components according to the invention. The system is a blood collection and processing system. The system comprises a first container (14) for the collection of whole blood from a donor. The container (14) is connected to a collection tube (5) and to a transfer tube (2) via inlet ports (15, 16). The transfer tube (2) connects the collection container (14) with inlet port (15) of a storage container (17) for the storage of plasma. The plasma storage container (17) comprises two outlet ports (4), which may or may not be protected by tamper evident protectors (1). The collection container (14) is further connected, by means of an additional inlet port (15) and via a transfer tube (2), to a processing container (18). The transfer tube (2) is connected to the processing container (18) via an inlet port (16). The processing container (18) is furthermore connected via an inlet port (15), transfer tubes (2a, 2b) and a red cell leukocyte filter (19) to a storage container (20) for the storage of red blood cells. The red blood cell storage container (20) may comprise an additive solution, such as SAG-M. The red blood cell storage container (20) comprises two outlet ports (4), which may or may not be protected by tamper evident protectors (1). The red blood cell container (20) may comprise an additional inlet port (15), and may be connected to further transfer tubing (2), as desired.

Optionally, the collection tube (5) is further connected to a needle (9) via a needle hub (10). Optionally, a bacteria diversion pouch (21) may be connected to the collection tube (5). The containers (14, 17, 18, 20) may comprise labels (22a, 22b, 22c, 22d).

In one embodiment, the system is used for the collection of whole blood. The system includes a needle (9) for donor venipuncture. The system allows for sterile venipuncture. Blood can be collected in a container (14) containing a calcium chelating agent to establish anticoagulation. The resistance through the needle (9), collection tube (5) and in the collection container (14) is low enough to establish, with the diastolic pressure of the donor, the collection of blood within the time it takes for the blood to clot. Preferably, the amount of air is limited so that no air-induced hemolysis occurs. Preferably, no turbulence is induced so that no turbulence-induced hemolysis occurs. Preferably, the inner surface of the container (14) is vast enough to collect up to 500 ml of blood without increase of the internal pressure, and no internal surface cleavage occurs. Preferably, the surfaces of the tube (5) and container (14) do not initiate severe activation of the blood platelets and plasma coagulation factors. For example, the system allows for manual or automated mixing during collection to ensure complete and immediate anticoagulation of the collected blood.

Typical amounts of anticoagulant range between 63 and 70 ml but can be different based on the collection volume.

It is preferred that the needle (9) and collection tube (5) are separated from the collection container (14) after the procedure has been completed to protect donor, physician, patient, and the unit of blood. It is then preferred that the collection tube (5) and needle (9) can be separated without a risk for leakage or bacterial contamination. Preferably, the tube (5) is sealed via a heat seal, or even more preferably, when PVC is the major constituent of the tube (5), via the application of a high-frequency seal. In general, tubes (2), typically made of plasticized PVC, are used to transfer whole blood or blood components from one part of the system to another part of the system. Tubes (2) typically are connected to other components by means of solvents rather than glue. It is highly preferred that the connections meet ISO3826 requirements.

The collection container (14) preferably is flexible, such that it contains no volume other than the anticoagulant before collection, but is able to expand to allow for the collection of the desired volume. The tube (5) and container (14) can allow for the detection and inspection of the contents. If the container is also indicated for the transfusion of blood, the container can be fitted with spike ports and a protective (but removable) cap that allows for the spike port to remain sterile until puncture.

Just like the other bags in a blood processing system, the container (14) can be provided with a label, such as a label containing (ISBT) relevant information such as production date, expiray date, reference number, lot number etc and indications for proper handling. Collection container (14) can have tube and/or injection molded components on either its top and/or bottom side, as desired, depending on the processing procedure of the particular blood bank and/or separation procedures in place.

In a preferred embodiment, the collection tube (5) is fitted with a diversion path and a diversion pouch (21) to collect the first volume of blood that contains skin from the donor's puncture wound and skin bacteria. After diversion of a first sample the passage of blood can be re-directed to the collection container (14). The tube to the diversion pouch preferably is provided with an irreversible or non-re-openable pinch clamp to avoid any flow back to the collection tube (5) after having taken a blood sample.

It may be desired that the collection container (14) is not indicated for the direct transfusion of the volume, but is fitted with one or more additional port entries (15, 16) that connect the collection container (14) to processing (18) and storage containers (17, 20, 24, 25) and filters via tubing (2).

Ports (15, 16, 4) can be designed such that no blood flow occurs during collection, but blood flow may be established in a later stage. To that end, ports may contain bag break-off parts or a Compoflow closure device. Ports (15, 16, 4) in containers (14, 17, 18, 20, 23, 24, 25, 26), such as flexible containers, can be tubes or tube inserts and/or injection molded components, allowing for fluid flow into or out of the container (14, 17, 18, 20, 23, 24, 25, 26). The injection molded components can have a closure device that disables the flow of blood components until needed. Opening of this closure device can be achieved manually or automatically. A feature typically comprised in addition on storage containers (17, 20, 24, 25) is one or more spike ports, representing outlet ports (4) used for transfusion purposes.

After separation of the collection set, the system can be folded in such a way that it can be placed into a centrifuge cup. Once all cups of the centrifuge have been filled, the units can be centrifugated to create layers of blood components. Typical centrifugation procedures are the BuffyCoat (BC) or Platelet Rich Plasma (PRP) method. For example, the system in FIG. 1 is optimized for the BC method but the system can be adapted to deal with other centrifugation procedures.

After centrifugation, plasma can be transferred to container (17) via one or more tubes (2), such as PVC-tubes, with or without Y-piece. The red cell additive (storage) solution comprised in container (20) can be led through the leukocyte depletion filter (19) into the processing container (18). It can be decided to let the BC inside the collection container (14) for further processing in a later stage. After having mixed the unit of red blood cells thoroughly and carefully with the additive solution, the resuspended red cells are filtrated back into red cell storage container (20) by means of gravity. Subsequently, the filtrated unit can be stored can be stored between 4-6° C. for a period of 6 or 7 weeks, depending on the type of storage container and the type of additive solution.

Where connectors are used, the connector may be a Y-piece.

Additional component/system components can be selected from the group consisting of an outlet port (4), preferably a spike port, an inlet port (15, 16), preferably a tube insert or breaker port, an adapter, a spike, a seal, a valve, a tube (2, 5), and a label (22), preferably a primary blood bag label.

Figure 3:
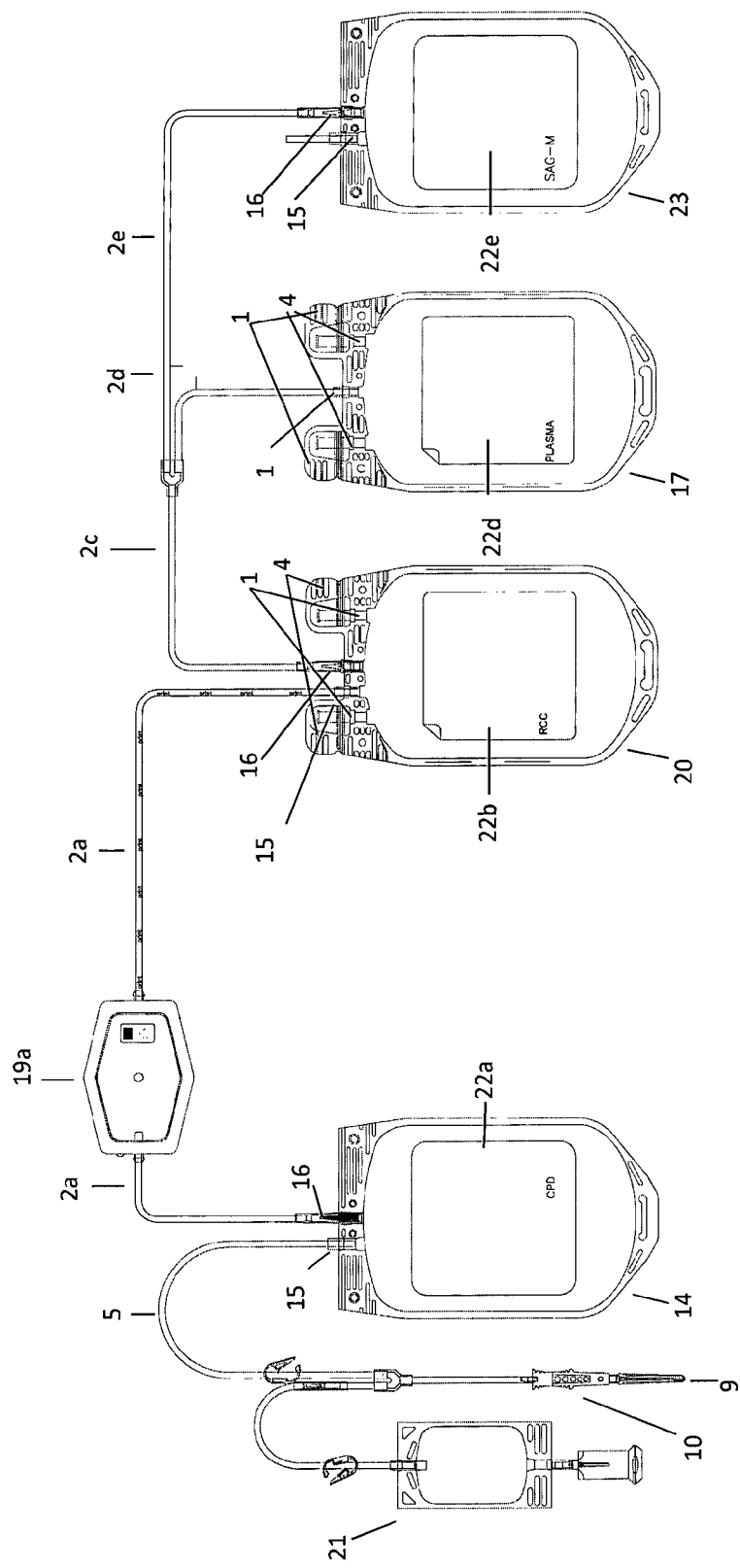
FIG. 3 shows an exemplary system according to the invention.

FIG. 3 shows a non-limiting exemplary system according to the invention, comprising containers and system components according to the invention. The system is a blood collection and processing system. The system comprises a first container (14) for the collection of whole blood from a donor. The container (14) is connected to a collection tube (5) via inlet port (15) and to a transfer tube via inlet port (16). The transfer tube (2a, 2b) connects the collection container (14) via a whole blood leukocyte reduction filter (19a) to a storage container (20) for the storage of red blood cells. The red blood cell storage container (20) comprises two outlet ports (4), which may or may not be protected by tamper evident protectors (1). The red blood cell container (20) comprises an additional inlet port (16) and is connected to transfer tubing (2c). Transfer tubing (2c) is further connected to transfer tubes (2d, 2e) via a connector. Transfer tubing (2d) connects the red blood cell storage container (20) with inlet port (15) of plasma storage container (17) comprising two outlet ports (4), which may or may not be protected by tamper evident protectors (1). Tubing (2e) connects the red blood cell storage container (20) with inlet port (16) of a further container (23), which comprises an additive solution, such as SAG-M. The container (23) may comprise an additional inlet port (15).

Optionally, the collection tube (5) is further connected to a needle (9) via a needle hub (10). Optionally, a bacteria diversion pouch (21) may be connected to the collection tube (5). The containers (14, 17, 20, 23) may comprise labels (22a, 22b, 22d, 22e).

In one embodiment, the system is used for the collection of whole blood. The system includes a needle (9) for donor venipuncture. The system allows for sterile venipuncture. Blood can be collected in a container (14) containing a calcium chelating agent to establish anticoagulation. The resistance through the needle (9), collection tube (5) and in the collection container (14) is low enough to establish, with the diastolic pressure of the donor, the collection of blood within the time it takes for the blood to clot. Preferably, the amount of air is limited so that no air-induced hemolysis occurs. Preferably, no turbulence is induced so that no turbulence-induced hemolysis occurs. Preferably, the inner surface of the container (14) is vast enough to collect up to 500 ml of blood without increase of the internal pressure, and no internal surface cleavage occurs. Preferably, the surfaces of the tube (5) and container (14) do not initiate severe activation of the blood platelets and plasma coagulation factors. For example, the system allows for manual or automated mixing during collection to ensure complete and immediate anticoagulation of the collected blood.

Typical amounts of anticoagulant range between 63 and 70 ml but can be different based on the collection volume.

It is preferred that the needle (9) and collection tube (5) are separated from the collection container (14) after the procedure has been completed to protect donor, physician, patient, and the unit of blood. It is then preferred that the collection tube (5) and needle (9) can be separated without a risk for leakage or bacterial contamination. Preferably, the tube (5) is sealed via a heat seal, or even more preferably, when PVC is the major constituent of the tube (5), via the application of a high-frequency seal. In general, tubes (2), typically made of plasticized PVC, are used to transfer whole blood or blood components from one part of the system to another part of the system. Tubes (2) typically are connected to other components by means of solvents rather than glue. It is highly preferred that the connections meet ISO3826 requirements.

The collection container (14) preferably is flexible, such that it contains no volume other than the anticoagulant before collection, but is able to expand to allow for the collection of the desired volume. The tube (5) and container (14) can allow for the detection and inspection of the contents. If the container is also indicated for the transfusion of blood, the container can be fitted with spike ports and a protective (but removable) cap that allows for the spike port to remain sterile until puncture.

Just like the other bags in a blood processing system, the container (14) can be provided with a label, such as a label containing (ISBT) relevant information such as production date, expiry date, reference number, lot number etc and indications for proper handling.

Collection container (14) can have tube and/or injection molded components on either its top and/or bottom side, as desired, depending on the processing procedure of the particular blood bank and/or separation procedures in place.

In a preferred embodiment, the collection tube (5) is fitted with a diversion path and a diversion pouch (21) to collect the first volume of blood that contains skin from the donor's puncture wound and skin bacteria. After diversion of a first sample the passage of blood can be re-directed to the collection container (14). The tube to the diversion pouch preferably is provided with an irreversible or non-re-openable pinch clamp to avoid any flow back to the collection tube (5) after having taken a blood sample.

It may be desired that the collection container (14) is not indicated for the direct transfusion of the volume, but is fitted with one or more additional port entries (15, 16) that connect the collection container (14) to processing (18) and storage containers (17, 20, 24, 25) and filters via tubing (2).

Ports (15, 16, 4) can be designed such that no blood flow occurs during collection, but blood flow may be established in a later stage. To that end, ports may contain bag break-off parts or a Compoflow closure device. Ports (15, 16, 4) in containers (14, 17, 18, 20, 23, 24, 25, 26), such as flexible containers, can be tubes or tube inserts and/or injection molded components, allowing for fluid flow into or out of the container (14, 17, 18, 20, 23, 24, 25, 26). The injection molded components can have a closure device that disables the flow of blood components until needed. Opening of this closure device can be achieved manually or automatically. A feature typically comprised in addition on storage containers (17, 20, 24, 25) is one or more spike ports, representing outlet ports (4) used for transfusion purposes.

Typically, the first step after collection is filtration during which leukocytes are depleted by means of filter (19a). Depending on the leukocyte filer used, platelets are allowed to pass through the filter or are also removed. Filtration is done under gravity conditions. The filtrate is collected in collection container (18), which typically is flexible.

After filtration, the system can be folded in such a way that it can be placed into a centrifuge cup. Once all cups have been filled (after balancing the cups that are opposite of each other), the units can be centrifuged to create layers of blood components, in particular red cells and plasma or in some cases red cells, plasma and platelets. The system shown in FIG. 3 is optimized for the preparation of red cells and plasma without leukocytes and platelets. Plasma is transferred to bag 20 and the red cells remain in collection container (14) and in a subsequent step is diluted with additive solution. After thorough but careful mixing, the resuspended red cells are filtrated back into storage container (20) by means of gravity. The filtrated unit can be stored between 4-6° C. for a period of 6 or 7 weeks, depending on the type of storage container and the type of additive solution.

Where connectors are used, the connector may be a Y-piece.

Additional component/system components can be selected from the group consisting of an outlet port (4), preferably a spike port, an inlet port (15, 16), preferably a tube insert or breaker port, an adapter, a spike, a seal, a valve, a tube (2, 5), and a label (22), preferably a primary blood bag label.

Figure 4:
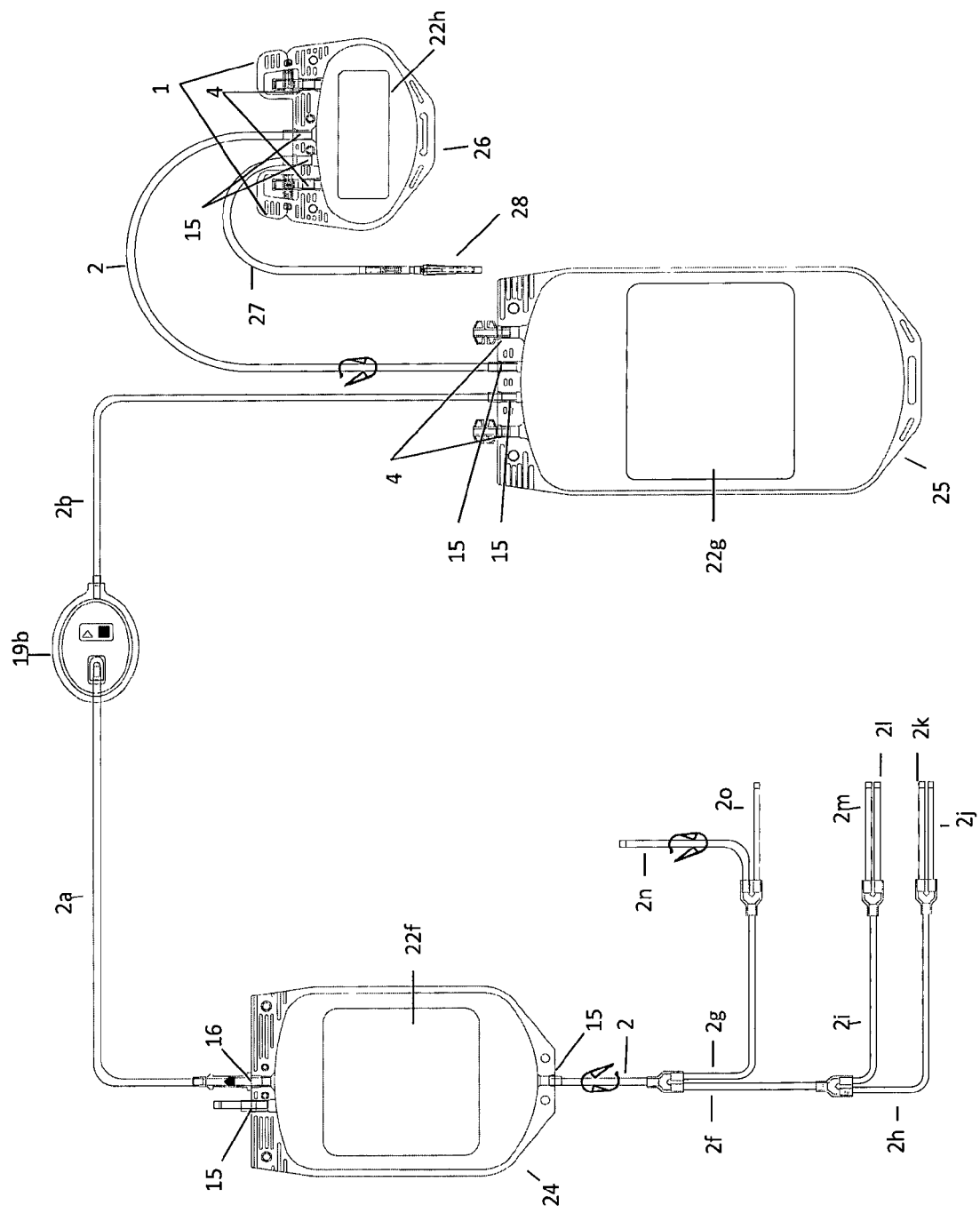
FIG. 4 shows an exemplary system according to the invention.

FIG. 4 shows a non-limiting exemplary system according to the invention, comprising containers and system components according to the invention. The system is a system for the processing of platelets. A typical platelet processing system, as shown in FIG. 4, comprises tubes to connect single units of platelets, optionally via a pool or collection container (24) and/or a leukocyte depletion filter (19b), to a platelet storage container (25). The tubes may enable the connection of single units of platelets and an additive solution. In a preferred embodiment, the system is fitted for the leukocyte removal via filtration of platelet pools. The single units of platelets may be comprised, e.g., in collection containers (14) that may or may not be part of the system. The system preferably also comprises a sampling bag (26) and/or sampling point (28), attached directly or indirectly (via tube (27) to sample bag (26)). All connections can be made by means of tubes. In some cases, connectors, such as Y-pieces, may be required to establish the correct connections. A typical pool of platelets consists of 4, 5 or 6 single units of platelets, depending on the number of platelets per unit/platelet concentration, the type of storage container and the additive solution.

Accordingly, the system of FIG. 4 comprises a transfer tubing (2), and optionally a collection container (24) for the collection of buffy coats and plasma. If collection container (24) is present, it is connected via an inlet port (16) to the transfer tubing (2). The transfer tubing (2) is connected via a connector to further transfer tubes, such as transfer tubes (2f, 2g). Transfer tube (2f) can be connected via a connector to transfer tubes (2h, 2i). Transfer tubes (2h, 2i) can be connected via connectors to transfer tubes (2j, 2k and 2l, 2m). These may in turn be connected to a number, such as 4, of sterile docked collection containers (14), not shown. In general, the number of transfer tubes and collection containers may vary. Transfer tubing (2g) can be connected via a connector, to transfer tubes (2o, 2p). These may in turn be connected to a sterile docked collection container (14) and to a plasma container (17), not shown. In the alternative, a plasma container (17) may be docked to one of transfer tubes (2j, 2k and 2l, 2m), and 2 collection containers (14) may be docked to transfer tubes (2o, 2p). The optional collection container (24) further comprises inlet ports (15, 16). Transfer tubes (2a, 2b) provide a connection to to inlet port (15) of platelet storage container (25), optionally via a platelet leukocyte reduction filter (19b). The platelet storage container (25) comprises two outlet ports (4), which may or may not be protected by tamper evident protectors (1). The platelet storage container (25) may further be connected via inlet port (15) and transfer tubing (2) to inlet port (15) of a sampling container (26) comprising two outlet ports (4), which may or may not be protected by tamper evident protectors (1). Sampling container (25) may further comprise an inlet port (15) connected to a sampling tube (27).

The containers (24, 25, 26) may comprise labels (22f, 22g, 22h).

Where connectors are used, the connector may be a Y-piece.

This type of system is designed to function on automatic blood component separation equipment but in principle, filtration can also be performed under gravity conditions although this procedure usually requires an adapted filter product.

Additional component/system components can be selected from the group consisting of an outlet port (4), preferably a spike port, an inlet port (15, 16), preferably a tube insert or breaker port, an adapter, a spike, a seal, a valve, a tube (2, 5), and a label (22), preferably a primary blood bag label.

Figure 5:
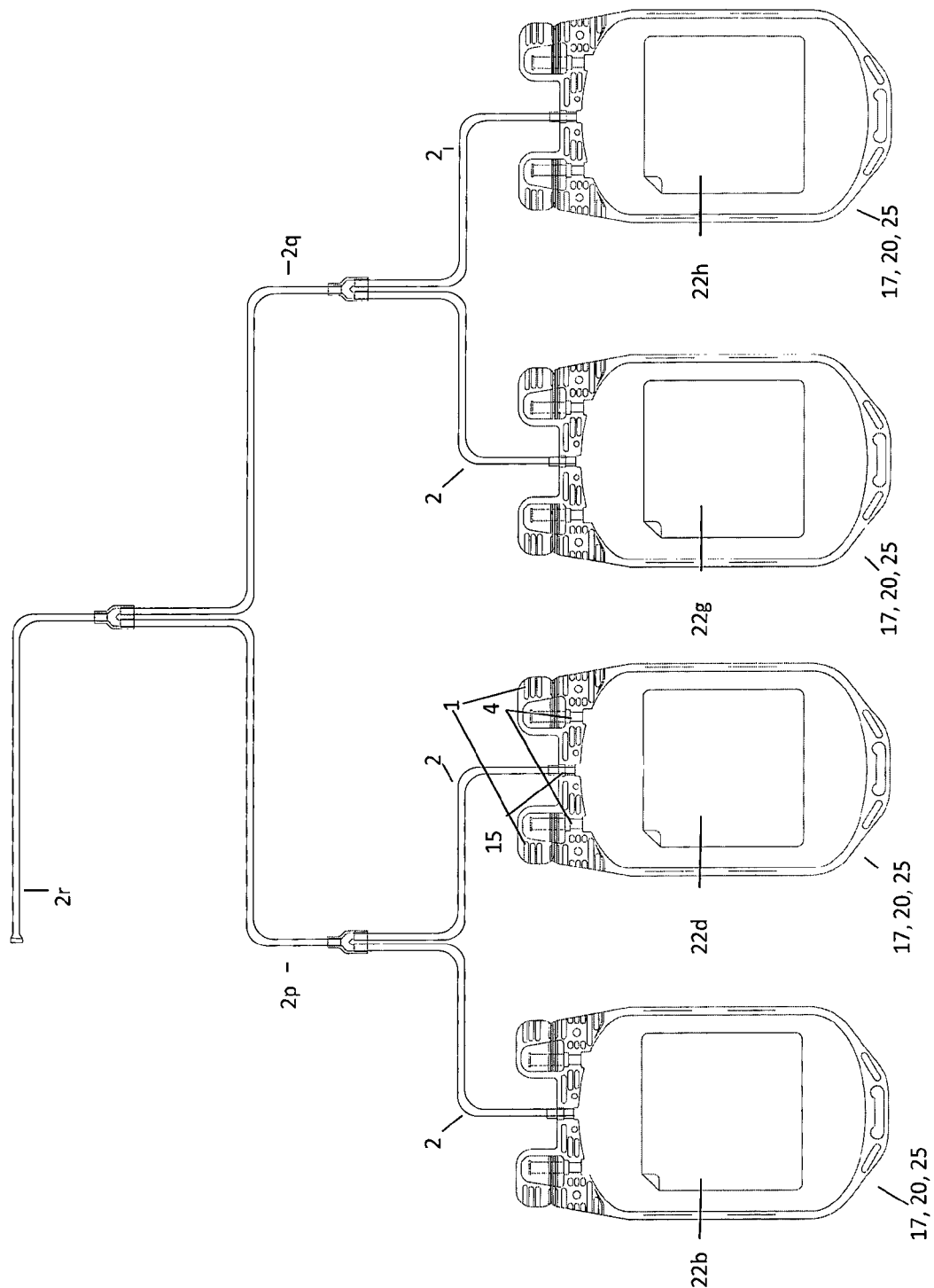
FIG. 5 shows an exemplary system according to the invention.

FIG. 5 shows a non-limiting exemplary system according to the invention, comprising containers and system components according to the invention. The system is a pediatric transfusion system. The system comprises more than 1, e.g. 2, 3, or 4 (as shown in FIG. 5) storage containers (17, 20, 25) for storing blood components such as plasma, red blood cells or platelets. Each of the storage containers comprises two outlet ports (4), which may or may not be protected by tamper evident protectors (1). Each of the storage containers (17, 20, 25) comprises at least one inlet port (15) connected with a transfer tube (2). Outlet ports, tamper evident protectors and inlet ports are labeled with reference signs for one exemplary storage container in FIG. 5. The transfer tubes (2) may be connected via connectors with further transfer tubes (2p, 2q). The further transfer tubes (2p, 2q) may be connected with transfer tube (2r) via a connector. Transfer tube (2r) may be in sterile connection with a further storage container (17, 20, 25) comprising plasma, red blood cells or platelets (not shown). The system allows to reduce the blood components volume typically obtained from an adult donor by transferring it to more than one storage container.

The containers (17, 20, 25) may comprise labels (22b, 22d, 22g).

In one embodiment, the system is used for the processing and storage of pediatric units of red cells, plasma or platelets. The system typically includes four PVC containers according to the invention (17, 20, 25) which are connected to each other by means of tubing (2) and injection molded components such as Y-pieces. Typical applications are the transfusions of red cells, plasma or platelets for small children or neonates. All containers (17, 20, 25) have one or more spike ports (4) for transfusion purposes.

Where connectors are used, the connector may be a Y-piece.

Additional component/system components can be selected from the group consisting of an outlet port (4), preferably a spike port, an inlet port (15, 16), preferably a tube insert or breaker port, an adapter, a spike, a seal, a valve, a tube (2, 5), and a label (22), preferably a primary blood bag label.

In a highly preferred embodiment, the system is any system as described above, wherein the container (14) for the collection of whole blood and intended for centrifuge separation of the whole blood, comprises ATBC and at least one of DEHT, DINCH; BTHC and pentaerythritol tetravalerate. The container comprising red cells, or a red cell product, (20) comprises an extractable agent that has non-polar alkyl chains of individual length C8 or greater, being DINCH (or DEHCH) or DEHT. Accordingly a combination of DINCH or DEHT as the first extractable agent with DEHT, DINCH; ATBC, BTHC or pentaerythritol tetravalerate as the second extractable agent is preferred for this container, wherein the first and second extractable agents are different from each other. The container comprising platelets, or a platelet product, (25) comprises DINCH, BTHC, or pentaerythritol tetravalerate.

Accordingly, the first extractable agent may be selected from DINCH, BTHC and pentaerythritol tetravalerate, and the second extractable agent may be selected from DINCH, BTHC, pentaerythritol tetravalerate, DEHT and ATBC, wherein the first and second extractable agent are different from each other. The container comprising plasma, or a plasma product, (17) comprises DINCH, DEHT or a combination thereof as low-leaching entities.

Also preferably, the tubes comprise DEHT and ATBC. Also preferably, injection-molded components comprise DINCH and ATBC.

Blood Component Products

The present invention also provides for blood component products. The blood component products comprise a blood component such as RBCs, plasma or platelets in a container according to the invention. The blood component product may further comprise an additive solution, especially if the blood component is red blood cells.

As explained before, DEHP is known to exert a beneficial effect on blood components, in particular RBCs, and to inhibit hemolysis. DEHP has been shown to work well with and support the action of commercially available additive solutions such as SAG-M or AS-1.

Thus, if DEHP-free or phthalate-free containers and systems according to the invention are to be used, it is beneficial to compensate for the action of DEHP by using specific extractable agents, or well-balanced combinations of extractable agents and additive solutions. The right combination of extractable agent and additive solution has the advantage of good quality blood components without the negative effects of leaching phthalate.

Thus, the invention provides a blood component product, the blood component product comprising:
 (a) a container,
 (b) a blood component, and optionally
 (c) an additive solution.

The container is according to the invention, as described in detail above. In particular, the above descriptions of preferred extractable agents and combinations thereof apply.

The blood component product according to the invention comprises about 1% or less than about 1% (w/w) of DEHP.

For example, the blood component product comprises about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

More preferably, the blood component product comprises about 1% or less than about 1% (w/w) of phthalates. For example, the blood component product comprises about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalates.

Preferably, the blood component, or the blood component and additive solution comprised in the container of the blood component product comprise less than 10 ppm DEHP, less than 8 ppm DEHP, preferably less than 5 ppm DEHP or more preferably less than 3 ppm DEHP, such as 0 ppm DEHP. It is even more preferred that the blood component, or the blood component and additive solution comprised in the container of the blood component product comprise less than 10 ppm phthalate, less than 8 ppm phthalate, preferably less than 5 ppm phthalate or more preferably less than 3 ppm phthalate, such as 0 ppm phthalate.

It is more preferred that the blood component, or the blood component and additive solution comprised in the blood component product are DEHP-free. Most preferably, the blood component, or the blood component and additive solution in the blood component product are phthalate-free.

Most preferably, the blood component product is DEHP-free, or is phthalate-free.

The blood component can be red blood cells, plasma or platelets.

In the collection and processing of blood and blood products, it is typical to remove leukocytes from, or at least reduce the number of leukocytes in, the blood components prior to their storage and transfusion. RBCs suspended in an additive solution, as well as platelets suspended in plasma or in a plasma additive solution, are often subjected to a leukocyte reduction step which commonly includes filtration of the cells/additive solution. Thus, RBCs and platelets can be subjected to a filtration step or other treatment whereby leukocytes and/or other undesirable agents or pathogens such as prions are substantially removed (or the populations of leukocytes and/or prions are substantially reduced) from the RBCs. In one embodiment, concentrated RBCs may be combined with an additive solution and the combined concentrated RBC/additive solution composition may be subjected to the leukocyte and/or prion removal (e.g., filtration) step.

Preferred blood component products for these different blood components are described in further detail below.

Red Blood Cell Products

In one aspect, the invention provides a blood component product comprising red blood cells. The blood component product comprises an additive solution. Typically, the additive solution comprises a nutrient and a buffer. The red blood cells can be intended for transfusion to a patient.

The red blood cells can be red blood cell concentrates. Concentrated RBCs can be derived from whole blood either by manual or automated separation collection techniques which are known to those skilled in the art. RBC concentrates may include some residual amount of plasma. In one embodiment, the RBC concentrate may have most of its plasma removed as described, for example, in WO 2011/049709, incorporated herein by reference.

The RBC may include concentrated RBCs that have typically been combined with an additive solution selected to maintain cell function and metabolism of the RBCs during prolonged storage (e.g., at least about 42 days and possibly even up to at least 49 and/or 56 days).

RBCs, such as concentrated RBCs with some or most of the plasma removed are combined with additive solutions to provide a composition. The RBC composition may for example include between about 80 ml to about 150 ml of the additive solution combined with about 180 ml to about 250 ml of the concentrated RBCs. More preferably, the volume of additive solution may be about 100 ml to about 110 ml.

The red blood cells and the additive solution are comprised in a container according to the invention. The container can be any container according to the invention as described in detail above. In particular, the above descriptions of preferred extractable agents and combinations thereof apply.

Accordingly, the container may comprise one or more container walls defining an interior chamber. The container walls may comprise one or more layers, the layers consisting of a composition comprising one or more polymeric materials and at least one extractable agent, more preferably at least two. The at least one or at least two extractable agents is/are selected from the group consisting of a terephthalate ester, a cyclohexane dicarboxylic acid ester, a citrate ester, and a polyol ester. Preferably, the container further comprises one or more additional components besides the container wall(s) defining the interior chamber. It is also preferred that the polymeric material is PVC.

Importantly, the container comprises about 3% or less than about 3% (w/w) of DEHP. For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

The container may comprise about 3% or less than about 3% (w/w) of phthalate. For example, the container comprises about 2.5% (w/w) or less, about 2% (w/w) or less, about 1.5% (w/w) or less, preferably about 1% or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalate.

Even more preferably, the container is DEHP-free. Most preferably, the container is phthalate-free.

DEHP is of particular relevance for RBC storage, as it is extracted out of the plastic and becomes increasingly available for the RBCs: DEHP allows for an extended RBC storage of up to 42 days with current additive solutions SAGM and AS-1 (both containing saline, adenine, glucose, and mannitol).

The present invention suggests to compensate for the effect of DEHP on hemolysis reduction by using advantageous combinations of extractable agents, and advantageous combinations of extractable agents and additive solutions.

The compositions of the container (as described herein) that contacts the RBCs and the additive solution provide the RBCs with a storage environment that suppresses and otherwise maintains a low level of hemolysis. The action can be further enhanced by the choice of additive solution, as further explained below.

Isotonic or Hypotonic Additive Solutions

According to a first aspect, an additive solution is used that comprises a nutrient and a buffer. The additive solution may comprise one or more of the components selected from the group consisting of phosphate, guanosine, adenine, saline, citrate, gluconate, mannitol, and glucose. The solution may comprise a compound selected from guanosine, adenine or a combination thereof, and phosphate. The solution may comprise guanosine and/or adenine, phosphate and glucose. The solution may or may not contain saline. The solution may or may not contain mannitol. The solution may or may not contain citrate. The solution may or may not contain gluconate.

The additive solution can be phosphate buffered. Preferably, the solution is isotonic or hypotonic, more preferable isotonic or hypotonic and phosphate buffered.

Isotonic additive solutions have an effective osmolarity (i.e. tonicity) very similar to or identical with the osmolarity inside the red blood cell, so that the red blood cells neither swell (i.e. increase in cell volume) nor shrink (i.e. decrease in cell volume) in direct contact with the additive solution. An "isotonic additive solution" can be an additive solution exerting the osmotic pressure of 0.9% saline, and thus can be a composition exhibiting an effective osmolarity of about 300 mOsm.

Hypotonic as used herein means of an effective osmolarity lower than that inside the red blood cells, so that the cells have a tendency to swell (i.e. increase in cell volume) upon direct contact with the additive solution. A "hypotonic additive solution" can be an additive solution exerting less osmotic pressure than 0.9% saline, and thus can be a composition exhibiting an effective osmolarity of less than about 300 mOsm. The effective osmolarity may be less than about 250 mOsm, and may be even as low as about 200 mOsm.

The use of hypertonic additive solutions was long believed to inhibit hemolysis; however, a phosphate-buffered isotonic or hypotonic additive solution is now suggested to be even more beneficial to the red cell membrane and to offer the additional advantage that less compensation by hemolysis reducing agents such as DEHP is required. Hypotonic additive solutions, in particular hypotonic additive solutions having a pH of about 7.0 or lower, have been found to be particularly useful.

The isotonic or hypotonic additive solution can include between about 0 to 70 about mM of sodium chloride, about 1 mM to about 4.0 mM of adenine and/or guanosine; about 20 mM to about 60 mM of mannitol; about 2 mM to about 40 mM sodium citrate and/or citric acid; about 16 mM to about 30 mM sodium phosphate dibasic and/or monobasic, and about 20 mM to about 140 mM of glucose.

The pH of the additive solution can be acidic (below pH 7.0) or alkalic (above pH 8.0).

The additive solution may have a pH of about 7.0 or less. In particular, the additive solution can be an isotonic solution having a pH of about 7.0 or less, wherein preferably, the solution is phosphate-buffered.

Examples of suitable isotonic additive solutions include solutions comprising about 70 mM NaCl, about 50 mM glucose, about 1.4 mM adenine, about 1.4 mM guanosine, about 55 mM mannitol, about 8 mM sodium phosphate monobasic, about 16 mM sodium phosphate dibasic and a pH of about 5.7. Preferably, the solution is PAGGS-M.

Examples of suitable hypotonic additive solutions include solutions comprising about 50 mM glucose, about 1.4 mM adenine, about 1.4 mM guanosine, about 55 mM mannitol, about 8 mM sodium phosphate monobasic, about 16 mM sodium phosphate dibasic, and about 20-25 mM sodium citrate and/or citric acid, with a pH of <about 7.0 but ≥about 6.0. Preferably, the solution does not comprise chloride. Preferably, the solution is PAGGC-M.

In the alternative, the additive solution may have a pH of at least about 8.0. The additive solution can be a hypotonic additive solution having a pH of at least about 8.0, and preferably can be chloride-free. The hypotonic chloride-free additive solution can comprise: about 1 mM to about 2.2 mM adenine; about 20 mM to about 110 mM mannitol; about 2.2 mM to about 90 mM sodium citrate; about 16 mM to about 30 mM sodium phosphate dibasic; and about 20 mM to about 140 mM glucose. The hypotonic additive solution can be E-sol.

Further suitable additive solutions include any hypotonic additive solutions, such as described in U.S. Patent Publication Nos. US 2009/0239208 and US 2011/0117647, both of which are incorporated herein by reference.

Such additive solutions as described herein, in particular phosphate buffered isotonic and hypotonic additive solutions, have been found to compensate for the effects of DEHP and to reduce hemolysis of RBCs during processing and storage.

The additive solutions can be beneficially used with containers according to the invention; whose container walls may comprise one or more layers, the layers consisting of a composition comprising one or more polymeric materials and at least one extractable agent, the agent being selected from the group consisting of a terephthalate ester, a cyclohexane dicarboxylic acid ester, a citrate ester, and a polyol ester.

The skilled person understands that, albeit a second extractable agent is not required with these types of additive solutions, its beneficial effects may even be further enhanced if more than one extractable agent is present, as has been described in detail above, and as further described below.

Hypertonic Additive Solutions

In a second aspect, the additive solution comprises a nutrient and a buffer. The additive solution may be a hypertonic additive solution. Hypertonic as used herein means of an effective osmolarity higher than that inside the red blood cells, so that the cells have a tendency to shrink (i.e. decrease in cell volume) upon direct contact with the additive solution. A hypertonic solution can be a solution exerting a higher osmotic pressure than 0.9% saline, and thus can be a composition exhibiting an effective osmolarity of higher than about 300 mOsm.

SAGM and AS-1 (commercially available as Adsol) are preferred examples of hypertonic additive solutions. It was long believed that in order to inhibit hemolysis, hypertonic solutions could be useful. However, these solutions were believed to rely on compensation by leaching DEHP. It has now been found that surprisingly, also other extractable agents could be successfully used in combination with hypertonic additive solutions, making the need for DEHP obsolete.

The hypertonic additive solution may comprise saline, adenine, glucose and mannitol. The hypertonic additive solution may further comprise sodium chloride. Exemplary hypertonic additive solutions may comprise about 40 mM to about 120 mM glucose, about 1.2 to about 2.2 mM adenine, about 25 to about 45 mM mannitol, and may further comprise about 140 mM to 160 mM of sodium chloride.

A preferred additive solution is SAGM, comprising about 50 mM glucose, about 1.25 mM adenine, about 29 mM mannitol, and about 150 mM sodium chloride. Likewise preferred is AS-1, comprising about 110 mM glucose, about 2.0 mM adenine, about 42 mM mannitol, and about 150 mM sodium chloride.

For hypertonic additive solutions, it is preferred that the container according to the invention used is a container wherein the container wall(s) comprise at least two extractable agents. Preferably the second extractable agent is selected from the group consisting of a terephthalate ester, a cyclohexane dicarboxylic acid ester, a citrate ester, and a polyol ester.

Albeit also the use of a single extractable agent, such as in particular DINCH, can suppress hemolysis, it has been found that a combination of at least two extractable agents selected from the group consisting of a terephthalate ester, a cyclohexane dicarboxylic acid ester, a citrate ester, and a polyol ester exerted a beneficial interaction with the hypertonic additive solution, thereby efficiently reducing hemolysis also in the absence of DEHP. The effect of a combination of at least two extractable agents was found to be superior and more than additive. While the present extractable agents allow for the use of isotonic and hypotonic additive solutions in the presence of a single extractable agent, the skilled person will understand that the use of more than one extractable agent, as described below, is also advantageous in combination with these solutions, and may help to further reduce hemolysis.

The at least two extractable agents can be comprised in the composition of the same layer, or can be comprised in the compositions of different layers. For example, the container can be a container wherein the composition of one or more of the layers comprises a second extractable agent, preferably a second extractable agent selected from the group consisting of a terephthalate ester, a cyclohexane dicarboxylic acid ester, a citrate ester, and a polyol ester. For example, the one or more container walls can comprise at least a first layer and a second layer, wherein the first layer consists of a composition comprising one or more polymeric materials and at least one extractable agent selected from the group consisting of a terephthalate ester, a cyclohexane dicarboxylic acid ester, a citrate ester, and a polyol ester, wherein the second layer consists of a composition comprising one or more polymeric materials and at least one extractable agent selected from the group consisting of a terephthalate ester, a cyclohexane dicarboxylic acid ester, a citrate ester, and a polyol ester. Typically, the extractable agents comprised in the composition of the first and second layers are different from each other.

While several combinations of extractable agents have been shown to reduce hemolysis efficiently when combined with the above-described hypertonic additive solutions, SAG-M or AS-1, some combinations were found to be particularly useful.

For example, one extractable can be a cyclohexane dicarboxylic acid ester and one extractable agent is selected from the group consisting of a citrate ester, a terephthalate ester and a polyol ester. The cyclohexane dicarboxylic acid ester can be DINCH and the citrate ester can be ATBC. The cyclohexane dicarboxylic acid ester can be DINCH and the citrate ester can be BTHC. The cyclohexane dicarboxylic acid ester can be DINCH and the terephthalate ester can be DEHT. The cyclohexane dicarboxylic acid ester can be DINCH and the polyol ester can be pentaerythritol tetravalerate.

Combinations of DEHT with ATBC, of DEHT with BTHC and of DEHT with pentaerythritol tetravalerate are useful. However, combinations of DINCH with ATBC, BTHC, DEHT or pentaerythritol tetravalerate are even more preferred, a combination of DINCH and ATBC being most preferred.

The advantageous effects of a combination of DINCH with ATBC were observed over a wide range of DINCH to ATBC ratios, however were most pronounced when DINCH makes up for about 70% to about 90%, preferably about 75% to about 85%, more preferably about 80% (w/w) of the total weight of DINCH and ATBC, and ATBC makes up for about 30% to about 10%, preferably about 25% to about 15%, more preferably about 20% (w/w).

For a combination of DINCH with BTHC, the advantageous effects were also observed over a wide range of DINCH to BTHC ratios, however were most pronounced when DINCH makes up for about 40% to about 60%, preferably about 45% to about 55%, more preferably about 50% (w/w) of the total weight of DINCH and BTHC, and BTHC makes up for about 60% to about 40%, preferably about 55% to about 45%, more preferably about 50% (w/w). For a combination of DINCH and BTHC, synergistically improved gas permeability was observed.

Similar results were obtained for a combination of DINCH and pentaerythritol tetravalerate. Combinations of DINCH and pentaerythritol tetravalerate were found useful for a range of ratios, however particularly good results were obtained when DINCH makes up for about 50% to about 70%, preferably about 55% to about 65%, more preferably about 60% (w/w) of the total weight of DINCH and pentaerythritol tetravalerate, and pentaerythritol tetravalerate makes up for about 30% to about 50%, preferably about 35% to about 45%, more preferably about 40% (w/w).

The advantageous effects of a combination of DINCH with DEHT were also observed over a wide range of DINCH to DEHT ratios, however were most pronounced when DINCH makes up for about 50% to about 70%, preferably about 55% to about 65%, more preferably about 60% (w/w) of the total weight of DINCH and DEHT, and DEHT makes up for about 30% to about 50%, preferably about 35% to about 45%, more preferably about 40% (w/w).

Combinations of DEHT and ATBC have also been found useful, e.g. when DEHT makes up for about 50% to about 70%, preferably about 55% to about 65%, more preferably about 60% (w/w) of the total weight of DEHT and ATBC, and ATBC makes up for about 30% to about 50%, preferably about 35% to about 45%, more preferably about 40% (w/w).

Combinations of DEHT and BTHC have also been found useful, e.g. when DEHT makes up for about 40% to about 60%, preferably about 45% to about 55%, more preferably about 50% (w/w) of the total weight of DEHT and BTHC, and BTHC makes up for about 60% to about 40%, preferably about 55% to about 45%, more preferably about 50% (w/w).

Combinations of DEHT and pentaerythritol tetravalerate were found useful as well, for a range of ratios, however particularly good results were obtained when DEHT makes up for about 40% to about 60%, preferably about 45% to about 55%, more preferably about 50% (w/w) of the total weight of DEHT and pentaerythritol tetravalerate, and pentaerythritol tetravalerate makes up for about 60% to about 40%, preferably about 55% to about 45%, more preferably about 50% (w/w).

Useful and preferred combinations of extractable agents have also been described in further detail above, and in the description throughout.

In one aspect, the present disclosure is directed to a red blood cell product that includes a container according to the invention having one or more container wall(s) defining an interior chamber. The container wall is made of a composition that includes a polymeric material, preferably PVC, and at least one extractable agent that is or includes a terephthalate ester, cyclohexane dicarboxylic acid ester, citrate ester, or polyol ester in an amount or in amounts effective to suppress hemolysis in red blood cells. A suspension of red blood cells is contained within the interior chamber and includes concentrated red blood cells and an additive solution that includes a nutrient and a buffer. Preferably, the additive is isotonic or hypotonic. Preferably, the container is DEHP-free, more preferably, phthalate-free. Preferably, the red blood cell product is DEHP-free, more preferably, phthalate-free.

In one aspect, the present disclosure is directed to a red blood cell product that includes a container according to the invention having one or more container wall(s) defining an interior chamber. The container wall(s) is (are) made of a composition that includes a polymeric material, preferably PVC, and at least two extractable agents that include a terephthalate ester, cyclohexane dicarboxylic acid ester, citrate ester, or polyol ester in amounts effective to suppress hemolysis in red blood cells. The polymeric material(s) incorporate(s) this or these extractable agent(s) in a single or multiple layers that each may include one or more of these extractable agents. A suspension of red blood cells is contained within the interior chamber and includes concentrated red blood cells and SAGM, Adsol, or an additive solution that includes a nutrient and a buffer. Preferably, the container is DEHP-free, more preferably, phthalate-free. Preferably, the red blood cell product is DEHP-free, more preferably, phthalate-free.

Plasma Products

In one aspect, the invention provides a blood component product comprising plasma. An additive solution may be used but is not required. The plasma can be intended for transfusion to a patient.

The plasma is comprised in a container according to the invention, as described in detail above.

Accordingly, the container may comprise one or more container walls defining an interior chamber. The container walls may comprise one or more layers, the layers consisting of a composition comprising one or more polymeric materials, preferably PVC, and at least one extractable agent. The extractable agent is selected from the group consisting of a terephthalate ester, a cyclohexane dicarboxylic acid ester, a citrate ester, and a polyol ester. Preferably, the container further comprises one or more additional components besides the container wall(s) defining the interior chamber.

Importantly, the container comprises about 3% or less than about 3% (w/w) of DEHP.

For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less, about 0.0001% or less, or about 0.0000% (w/w) of DEHP.

The container may comprise about 3% or less than about 3% (w/w) of phthalate. For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalate.

Even more preferably, the container is DEHP-free. Most preferably, the container is phthalate-free.

Containers of the invention have been described in more detail above, and can be used for the present blood component product. In particular, the above descriptions of preferred extractable agents and combinations thereof apply.

Hemolysis is not an issue with plasma as the blood component; therefore, leaching of extractable agents into the plasma comprised in the container does not provide an advantage. Consequently, the presence of DEHP or phthalates is even less desirable.

Also, preferably the at least one extractable agent is less leaching than DEHP. This is the case in particular for DINCH and DEHT, which accordingly are preferred in this application. Moreover, these extractable agents, as well as BTHC and pentaerythritol tetravalerate have been found to allow for a formulation having a glass transition temperature that is equivalent or lower than that of PVC-DEHP. Not all extractable agents allow for an equal quality in homogenization, so again, from a technical perspective (i.e. to reach the theoretical glass transition temperature), the combining of two or more extractable agents is advantageous. This holds true in particular for plasma products, since storage typically is at low temperatures of about −80° C. (initial freezing) or at about −20° C. to about −40° C. (long-term storage). TOTM and/or ESO may be added as well.

In one aspect, the present disclosure is directed to a plasma product that includes a container according to the invention having one or more container wall(s) defining an interior chamber. The container wall is made of a composition that includes a polymeric material, preferably PVC, and at least one extractable agent, preferably at least two extractable agents, that lower(s) the glass transition temperature of that polymeric material and that is or includes a terephthalate ester, cyclohexane dicarboxylic acid ester, citrate ester, or polyol ester in an amount or in amounts effective to keep plasma frozen for a longer period of time, typically up to two years. The polymeric material incorporates this or these extractable agent in a single or multiple layers that each may include one or more of these extractable agents. Preferably, container is DEHP-free, more preferably, phthalate-free. Preferably, the plasma product is DEHP-free, more preferably, phthalate-free.

Platelet Products

In one aspect, the invention provides a blood component product comprising platelets. An additive solution may be used but is not required. If desired, plasma, preferably autologous plasma, can be admixed to the platelets. The platelets can be intended for transfusion to a patient. The platelets can be single platelet concentrates.

The platelets are comprised in a container according to the invention. The container has been described in detail above.

Accordingly, the container may comprise one or more container walls defining an interior chamber. The container walls may comprise one or more layers, the layers consisting of a composition comprising one or more polymeric materials, preferably PVC, and at least one extractable agent. The extractable agent is selected from the group consisting of a terephthalate ester, a cyclohexane dicarboxylic acid ester, a citrate ester, and a polyol ester. Preferably, the container further comprises one or more additional components besides the container wall(s) defining the interior chamber.

The container may comprise about 3% or less than about 3% (w/w) of DEHP. For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of DEHP.

The container may comprise about % or less than about 3% (w/w) of phthalate. For example, the container comprises about 2.5% (w/w) or less, about 2% (w/w) or less, about 1.5% (w/w) or less, preferably about 1% (w/w) or less, about 0.75% (w/w) or less, more preferably about 0.5% (w/w) or less, about 0.4% (w/w) or less, about 0.3% (w/w) or less, about 0.25% (w/w) or less, about 0.2% (w/w) or less, about 0.15% (w/w) or less, about 0.1% (w/w) or less, about 0.01% (w/w) or less, about 0.001% (w/w) or less, about 0.0005% (w/w) or less about 0.0001% or less, or about 0.0000% (w/w) of phthalate.

Even more preferably, the container is DEHP-free. Most preferably, the container is phthalate-free.

Containers of the invention have been described in more detail above, and can be used for the present blood component product. In particular, the above descriptions of preferred extractable agents and combinations thereof apply.

Hemolysis is not an issue with platelets as the blood component; therefore, leaching of extractable agents into the plasma comprised in the container does not provide an advantage. Consequently, the presence of DEHP or phthalates is even less desirable. Also, preferably the at least one extractable agent is less leaching than DEHP.

Preferably, the container is gas-permeable for oxide and carbon dioxide. Gas permeability is improved with good homogenization of polymeric material, such as PVC, and extractable agent. Also, the integrity of container components such as adapters, tubes and the like is very relevant in this application, since platelets are typically stored non-frozen, e.g. at about 22° C., and therefore are more prone to bacterial contamination. Also, it is especially desirable for this application that any docked tubing is docked completely free of micro-leakages and bacterial contamination.

While all extractable agents from the group of terephthalate ester, cyclohexane dicarboxylic acid ester, citrate ester, and polyol ester were found to fulfill these requirements when used, in particular when used in combination with PVC, some extractable agents and combinations of extractable agents were found to yield particularly good homogenization and gas permeability properties. These include DINCH, BTHC and pentaerythritol tetravalerate. Accordingly, the first extractable agent may be selected from DINCH, BTHC and pentaerythritol tetravalerate, and the second extractable agent may be selected from DINCH, BTHC, pentaerythritol tetravalerate, DEHT and ATBC, wherein the first and second extractable agent are different from each other. For example, a combination of BTHC and DINCH was found to yield excellent homogenization and synergistically high oxygen permeability. Based on the molecular structure, a combination of DINCH and pentaerythritol tetravalerate yields equal opportunity. The above described combinations accordingly are highly preferred in this application.

In one aspect, the present disclosure is directed to a platelet product that includes a container according to the invention having one or more container wall(s) defining an interior chamber. The container wall is made of a composition that includes a polymeric material, preferably PVC, and at least one extractable agent, preferably at least two extractable agents, that acts as a gas-permeability increasing agent(s) and that is/are or include(s) a terephthalate ester, cyclohexane dicarboxylic acid ester, citrate ester, or polyol ester in an amount or in amounts effective that is suitable to store donor platelets up to 7 days after collection. The polymeric materials incorporate this or these extractable agents in a single or multiple layers that each may include one or more of these extractable agents. Preferably, the container is DEHP-free, more preferably, phthalate-free. Preferably, the platelet product is DEHP-free, more preferably, phthalate-free.

Methods and Uses, Kits

The present invention also provides for the use of the containers, system components and systems according to the invention for the ex vivo collection, processing and storage of blood or a blood component.

Further provided is a method of a method of administering a blood component to a patient in need thereof, the method comprising the steps of (a) providing a blood component product according to the invention and (b) administering the blood component or blood component and additive solution to said patient.

Also provided is a kit, the kit comprising at least one container, system component or system according to the invention, or a combination thereof. The kit can be a kit for manual blood processing. The kit may comprise further components, such as a needle for blood collection and/or a bacteria diversion pouch.

EXAMPLES

The following examples are not to be construed as limiting.

Example 1

To examine the impact of different extractable agents during blood component collection, processing and storage, leaching of different extractable agents was measured. The systems used were PVC-systems comprising DINCH or DEHT as extractable agent. The systems were compared to a PVC-system comprising DEHP as extractable agent, as typically used in the prior art.

Plasma was collected and stored in a PVC-DEHP (n=7) or PVC-DINCH or PVC-DEHT system. Extractable agent leaching was measured on day 1 (before freezing), after storage for 3 months, and after being thawed for 24 hrs after freezing.

The results are shown in Table 1 below.

TABLE 1

|  | PVC-DEHP(ppm) | PVC-DINCH(ppm) | PVC-DEHT(ppm) |
| --- | --- | --- | --- |
| Before freezing | 18.2 ± 11.1 | <1 | <1 |
| After thawing | 22.7 ± 1.9 | 0.8 ± 0.4 | 2.7 ± 0.4 |

TABLE 1-continued

|  | PVC-DEHP(ppm) | PVC-DINCH(ppm) | PVC-DEHT(ppm) |
|---|---|---|---|
| 24 h after thawing | 56.8 ± 20.0 | 4.5 ± 0.94 | 5.8 ± 1.0 |

It can be seen that the leaching observed for DINCH and DEHT is considerably lower than that for DEHP, resulting in a less contaminated blood product.

Moreover, Table 1 shows that DEHP leaching prior to storage (before freezing on day 1) accounts for a large part of the DEHP detected after storage for 3 month and 24 h after thawing. Leaching of DINCH and DEHT prior to storage (before freezing on day 1) is much less pronounced and accounts for a smaller portion of the respective extractable agent 24 h after thawing. The results emphasize the importance of avoiding blood product exposure to DEHP already prior to blood product storage.

Example 2

To investigate the impact of container components other than the container walls on DEHP leaching, single platelet concentrates were prepared from whole blood collected and stored for 12-16 h in a PVC system comprising DEHP. Subsequent storage was in a PVC-DEHT container with PVC-DEHP spike ports and tube inserts, and extractable agent leaching was measured on day 2 and day 6.

The results are shown in Table 2 below.

TABLE 2

|  | Day 2 | Day 6 |
|---|---|---|
| DEHT (ppm) | 9.7 ± 2.2 | 44.0 ± 11.0 |
| DEHP (ppm) | 22.4 ± 1.6 | 25.4 ± 3.0 |

The whole blood collection and storage for 12-16 hours cause an initial contamination with DEHP of >20 ppm. Already the presence of minor container components such as PVC-DEHP spike ports and tube inserts causes an increase of 3 ppm DEHP during storage.

Example 3

Red cells stored as red cell concentrates in two experimental PVC-DEHT containers without any DEHP contamination (n=6 for each group), after collection and whole blood storage (12-16 h) in PVC-DEHT. Systems were completely free of DEHP, and, if DEHT was not available, in some of the injection-molded components TOTM was used. Final DEHT leaching was around 4 ppm, whereas this normally is around 30 ppm for storage in PVC-DEHP.

Increased hemolysis observed in the absence of DEHP could be largely suppressed by using an isotonic, phosphate-buffered solution. See also Table 3.

TABLE 3

| Hemolysis | T3943 | T3948 |
|---|---|---|
| SAG-M | | |
| Day 35 | 0.69 ± 0.24 | 0.72 ± 0.35 |
| Day 42 | 0.97 ± 0.33 | 0.97 ± 0.42 |
| Day 49 | 1.46 ± 0.62 | 1.57 ± 0.72 |

TABLE 3-continued

| Hemolysis | T3943 | T3948 |
|---|---|---|
| PAGGS-M | | |
| Day 35 | 0.35 ± 0.18 | 0.45 ± 0.14 |
| Day 42 | 0.58 ± 0.28 | 0.55 ± 0.24 |
| Day 49 | 0.82 ± 0.38 | 0.81 ± 0.21 |

Example 4

Red cells stored as red cell concentrates in experimental PVC-DINCH containers without any DEHP contamination (n=8 for each group, after collection and whole blood storage (12-16 h) in PVC-DINCH. Systems were completely free of DEHP, and, if DINCH was not available, in some of the injection-molded components TOTM was used. Final DINCH leaching was around 5 ppm, whereas this normally is around 30 ppm for storage in PVC-DEHP. DINCH levels were undetectable in the PVC-DINCH systems on day 1 (i.e. after collection, whole blood storage for 12-16 hours, and processing) and 4 ppm in PVC-DEHP reference systems.

The absence of DEHP causes increased levels of hemolysis, which is completely suppressed by using an isotonic, phosphate-buffered solution. See also Table 4 below.

TABLE 4

| Bag system's material | Red Cell Additive Solution | Hemolysis rate day 42 |
|---|---|---|
| PVC-DINCH | PAGGS-M | 0.11% |
|  | SAG-M | 0.57% |
| Standard DEHP bags | SAG-M | 0.17% |

Example 5

Since in initial experiments (see e.g. example 4) it had been found that isotonic, phosphate-buffered additive solutions such as PAGGS-M completely suppressed hemolysis caused by the absence of DEHP, the beneficial interactions of specific combinations of extractable agents and additive solutions on hemolysis were further investigated.

A number of extractable agents and extractable agent combinations with additive solutions were found useful to suppress hemolysis. For several extractable agent and additive solution combinations, a more than additive effect was observed in the suppression of hemolysis. See also Table 5 below.

Red cells were stored as red cells concentrates in experimental non-DEHP containers in a paired study (n=4), after collection in systems with PVC-DEHP tubing and injection-molded components and PVC-BTHC sheeting and immediate processing thereafter, limiting the contamination of DEHP to <1 ppm in the final red cell product.

ATBC alone and DEHT alone, as a mono-extractable agent container, do not significantly suppress hemolysis when a hypertonic additive solution was used. Extractable agent blending significantly reduced hemolysis over DINCH as mono-extractable agent. See also Table 5 below. Similar observations were also made with a blend of DINCH and BTHC (50-50%) versus DINCH alone and BTHC alone.

TABLE 5

| Bag system's material | Red Cell Additive Solution | Hemolysis rate day 42 |
|---|---|---|
| PVC-DINCH | AS-1 | 0.47 ± 0.12% |
| PVC-DINCH/ATBC (~80-20%) | AS-1 | 0.25 ± 0.10% |
| PVC-DINCH/DEHT (~60-40%) | AS-1 | 0.31 ± 0.05% |

Example 6

Oxygen permeability measurements were performed of two mono-extractable agent foils and a dual-extractable agent foil. The choice of extractable agent significantly impacts the gas permeability of the final sheeting of a container. Theory does not state that all combinations of all extractable agents must perform synergistically towards a more favourable oxygen or carbon dioxide permeability. This depends on the solubility of the new blend towards these gases, as well as the positioning of the extractable agents towards one-another in the polymer matrix.

Thus, it was surprising that when blending DINCH and BTHC into a new compound, this blend did not present with an intermediate gas permeability, but with a gas permeability equal to or even higher than that of BTHC. Moreover, it was found that this new foil was perfectly homogenised, limiting the variation that the extrusion process may bring upon the gas permeability of a foil.

Results are presented in Table 6 below.

TABLE 6

| Material | $CO_2$ - 0% RH (cc/($m^2$ · 24 h)) | $O_2$ - 50% RH (cc/($m^2$ · 24 h)) |
|---|---|---|
| BTHC | 12714 | 2457 |
| DINCH | 7169 | 1330 |
| BTHC/DINCH (50/50%) | 12988 | 2719 |

Similar results were obtained when the experiment was repeated using a combination of DINCH and pentaerythritol tetravalerate.

Example 7

Since in initial experiments (see e.g. example 4) it had been found that isotonic, phosphate-buffered additive solutions such as PAGGS-M completely suppressed hemolysis caused by the absence of DEHP, in addition to the fact that high-pH, saline-free, hypotonic solutions are described to minimize the storage lesion, the opportunities to further improve on PAGGS-M while retaining the low pH property was further investigated.

Red cells were stored as red cell concentrates in PVC-TOTM containers to produce a storage environment completely free of DEHP or alternative extractable agent, in a paired study (n=7), after collection in systems with PVC-DEHP tubing and injection-molded components, limiting the level of DEHP at the end of storage to <4 ppm.

The results show that by introducing hypotonicity and removing the saline, hemolysis is suppressed at both day 42 and day 49 (p<0.01). However, because of the absence of an extracted hemolysis-suppressing agent, mean hemolysis still remains ≥0.4% on average, compared to a 0.2-0.3% that is the current expectation.

TABLE 7

| Bag system's material | Red Cell Additive Solution | Hemolysis rate day 42 | Hemolysis rate day 49 |
|---|---|---|---|
| PVC-TOTM | PAGGS-M | 0.54 ± 0.17% | 0.83 ± 0.26% |
| PVC-TOTM | PAGGC-M | 0.41 ± 0.15% | 0.65 ± 0.27% |

While the invention has been described in connection with various embodiments, it will be apparent to those skilled in the art that modifications and variations may be made thereto without departing from the spirit and scope of the invention.

The invention claimed is:

1. A container for blood or a blood component, the container comprising one or more container walls defining an interior chamber,
the container walls comprising one or more layers, the layers comprising a composition comprising polyvinyl chloride and extractable plasticizers consisting of a first, second and third extractable agents wherein said first extractable agent is di-2-ethylhexylterephthalate or a polyol ester, said second extractable agent is a cyclohexane dicarboxylic acid ester or a polyol ester, and said third extractable agent is a citrate ester or a polyol ester and optionally, one or more non-extractable agents selected from the group of TOTM, epoxidized soybean oil and epoxidized linseed oil, wherein each of said first, second and third extractable agents is different; and
wherein the container comprises less than about 3% (w/w) of phthalates.

2. The container according to claim 1, wherein the polyol ester is pentaerythritol tetravalerate, and the cyclohexane dicarboxylic acid ester is selected from the group consisting of 1,2-cyclohexyl dicarboxylic ester (DEHCH) and 1,2-cyclohexane dicarboxylic acid diisononyl ester (DINCH).

3. The container according to claim 1, wherein the container walls comprise at least a first layer and a second layer,
wherein the first layer consists of a composition comprising polyvinyl chloride and at least said first extractable agent,
wherein the second layer consists of a composition comprising polyvinyl chloride and at least said second extractable agent,
the container optionally comprising a third layer, the third layer consisting of a composition comprising one or more polymeric materials and at least said third extractable agent.

4. The container according to claim 1 wherein the first extractable agent is DEHT and the second extractable agent is DINCH, or wherein the first extractable agent is DEHT and the second extractable agent is pentaerythritol tetravalerate.

5. The container according to claim 1, comprising one or more additional container components comprising one or more polymeric materials and at least one extractable agent selected from the group consisting of a terephthalate ester, a cyclohexane dicarboxylic acid ester, a citrate ester, and a polyol ester,
wherein the additional components comprise less than about 3% (w/w) of DEHP.

6. The container according to claim 5, wherein the additional component comprises a composition comprising polyvinylchloride (PVC).

7. The container according to claim 5, wherein the composition of the one or more additional components comprises a second extractable agent selected from the group consisting of a terephthalate ester, a cyclohexane dicarboxylic acid ester, a citrate ester, and a polyol ester.

8. The container according to claim 7, wherein the first extractable agent in the composition of the one or more additional components comprises DEHT, and the second extractable agent in the composition of the one or more additional components is selected from the group consisting of ATBC or BTHC, DINCH, and pentaerythritol tetravalerate, or
wherein the first extractable agent in the composition of the one or more additional components is DINCH, and the second extractable agent in the composition of the one or more additional components is selected from the group consisting of ATBC or BTHC, DEHT, and pentaerythritol tetravalerate.

9. The container according to claim 5, wherein the additional component is selected from the group consisting of an outlet port, preferably a spike port, an inlet port, a tube insert or breaker port, an adapter, a spike, a seal, a valve, a tube, and a label, a primary blood bag label, and combinations thereof, and/or
wherein the additional component is an injection molded additional component, or an extruded additional component.

10. A blood component product, the blood component product comprising:
(a) a container according to claim 1,
(b) a blood component, and optionally
(c) an additive solution,
wherein the blood component product comprises less than about 3% (w/w) of DEHP,
wherein the blood component product comprises less than about 3% (w/w) of phthalates.

11. The blood component product according to claim 10, wherein the blood component is selected from the group consisting of red blood cells, plasma or platelets.

12. The blood component product according to claim 11, wherein the blood component is red blood cells and said additive solution a nutrient and a buffer.

13. The blood component product according to claim 12, wherein the additive solution is isotonic or hypotonic,
wherein the isotonic or hypotonic additive solution is phosphate buffered, wherein the additive solution is an isotonic phosphate buffered additive solution with a pH of about 7.0 or less, or a hypotonic phosphate buffered additive solution with a pH of about 7.0 or less or of at least about 8.0.

14. The blood component product according to claim 13, wherein the additive solution is an isotonic or hypotonic additive solution comprising about 0 mM to 70 about mM of sodium chloride, about 1 mM to about 4.0 mM of adenine and/or guanosine; about 20 mM to about 60 mM of mannitol; about 2 mM to about 40 mM of sodium citrate and/or citric acid; about 16 mM to about 30 mM of sodium phosphate dibasic and/or monobasic, and about 20 mM to about 140 mM of glucose,
wherein the additive solution is selected from PAGGS-M, PAGGC-M, and E-sol.

15. The blood component product according to claim 12, wherein the additive solution is a hypertonic additive solution and wherein the hypertonic additive solution,
is an additive solution comprising about 40 mM to about 120 mM glucose, about 1.2 mM to about 2.2 mM adenine, about 25 mM to about 45 mM mannitol, and about 140 mM to 160 mM of sodium chloride.

16. The blood component product according to claim 11, wherein the blood component is red blood cells and the container is a container comprising a combination of DENT and DINCH.

17. The container of claim 1 wherein said first extractable agent comprises DEHT and said second extractable agent comprises DINCH, and wherein said DEHT comprises about 30%-50% of said first and second extractable agents and said DINCH comprises about 50%-70% of said extractable agents.

18. The container of claim 17 wherein said DEHT comprises about 40% of said first and second extractable agents and said DINCH comprises about 60% of said extractable agents.

19. The container of claim 1 wherein said first extractable agent comprises DEHT and said second extractable agent comprises DINCH and said third extractable agent is selected from the group consisting of ATBC or ATHC.

20. A system component for a system for blood or blood component collection, processing, storage and/or transfusion, the system component comprising a composition comprising polyvinyl chloride and extractable plasticizers consisting of first, second and optional third agents wherein said first extractable agent is selected from the group consisting of di-2-ethyl hexyl terephthalate (DEHT), a citrate ester, and a polyol ester, said second extractable agent is selected from the group consisting of a cyclohexane dicarboxylic acid ester, a citrate ester, or a polyol ester, and said third extractable agent is selected from the group consisting of a terephthalate ester, a cyclohexane dicarboxylic acid ester, a citrate ester, or a polyol ester, and optionally, one or more non-extractable agents selected from the group of TOTM, epoxidized soybean oil and epoxidized linseed oil,
wherein the system component comprises less than about 3% (w/w) of DEHP, wherein the system component comprises less than about 3% (w/w) of phthalates.

21. The system component according to claim 20, wherein the cyclohexane dicarboxylic acid ester is selected from the group consisting of and 1,2-cyclohexane dicarboxylic acid diisononyl ester (DINCH) and 1,2-cyclohexyl dicarboxylic acid di-2-ethylhexyl ester (DEHCH), the citrate ester is selected from acetyl tributyl citrate (ATBC), acetyl trihexyl citrate (ATHC), and butyryl trihexyl citrate (BTHC), and the polyol ester is pentaerythritol tetravalerate.

22. The system component according to claim 20, wherein the system component is selected from the group consisting of an outlet port, a spike port, an inlet port preferably a tube insert or breaker port, an adapter, a spike, a seal, a valve, a tube, and a label, preferably a primary blood bag label, and combinations thereof, and/or
wherein the system component is an injection molded system component, or an extruded system component.

23. A system for blood or blood component collection, processing, storage and/or transfusion, the system comprising at least one system component according to claim 20,
wherein the system comprises less than about 3% (w/w) of di-2-ethylhexyl phthalate, wherein the system comprises less than about 3% (w/w) of phthalates.

* * * * *